(12) United States Patent
Speldrich et al.

(10) Patent No.: US 11,959,787 B2
(45) Date of Patent: Apr. 16, 2024

(54) FLOW SENSING DEVICE

(71) Applicant: Honeywell International Inc., Charlotte, NC (US)

(72) Inventors: Brian Speldrich, Charlotte, NC (US); Jamie Speldrich, Charlotte, NC (US); Paul Bey, Charlotte, NC (US); Scott Beck, Charlotte, NC (US); Ian Bentley, Charlotte, NC (US); Steven Lowery, Charlotte, NC (US); Richard Bishop, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/249,443

(22) Filed: Mar. 2, 2021

(65) Prior Publication Data

US 2022/0283007 A1  Sep. 8, 2022

(51) Int. Cl.
*G01F 1/684* (2006.01)
*B01L 3/00* (2006.01)
*G01F 1/69* (2006.01)

(52) U.S. Cl.
CPC .......... *G01F 1/6842* (2013.01); *G01F 1/684* (2013.01); *G01F 1/6845* (2013.01); *G01F 1/69* (2013.01); *A61M 2205/3331* (2013.01); *A61M 2205/3334* (2013.01); *B01L 3/5027* (2013.01); *B01L 3/502715* (2013.01)

(58) Field of Classification Search
CPC ...... G01F 1/6842; G01F 1/684; G01F 1/6845; G01F 1/69; A61M 2205/3331; A61M 2205/3334; B01L 3/5027; B01L 3/502715
See application file for complete search history.

(56) References Cited

U.S. PATENT DOCUMENTS

| 5,404,753 A * | 4/1995 | Hecht ................ G01F 1/6845 73/204.22 |
| 7,343,823 B2 * | 3/2008 | Speldrich ............. G01F 5/00 73/202 |
| 9,952,079 B2 * | 4/2018 | Speldrich ............. G01F 5/005 |
| 10,837,812 B2 | 11/2020 | Speldrich et al. |

(Continued)

FOREIGN PATENT DOCUMENTS

| CN | 101900625 A | 12/2010 |
| CN | 108141679 A | 6/2018 |

(Continued)

OTHER PUBLICATIONS

CN Office Action Mailed on Jun. 8, 2022 for CN Application No. 202210169625.

(Continued)

*Primary Examiner* — Ryan D Walsh
(74) *Attorney, Agent, or Firm* — Alston & Bird LLP

(57) ABSTRACT

Methods and apparatuses associated with flow sensing devices are provided. An example flow sensing device may include a sensing element disposed at least partially within the housing, and a plurality of channels disposed within the housing defining a flow path configured to convey a flowing media through the flow sensing device, wherein the flow path is disposed proximate the sensing element such that at least a portion of the flowing media makes direct contact with the sensing element.

6 Claims, 20 Drawing Sheets

(56) References Cited

U.S. PATENT DOCUMENTS

| | | | |
|---|---|---|---|
| 2002/0023485 A1* | 2/2002 | Kohmura | G01F 1/6842 73/202 |
| 2002/0078744 A1* | 6/2002 | Gehman | G01F 1/6845 73/204.11 |
| 2004/0118200 A1* | 6/2004 | Hornung | G01F 5/00 73/202 |
| 2004/0118218 A1* | 6/2004 | Mayer | G01F 1/6845 73/861.08 |
| 2004/0163463 A1* | 8/2004 | Ito | G01F 1/6845 73/204.26 |
| 2006/0033210 A1 | 2/2006 | Chauhan et al. | |
| 2010/0122583 A1 | 5/2010 | Rozgo et al. | |
| 2011/0247411 A1* | 10/2011 | Speldrich | G01F 5/005 29/527.1 |
| 2013/0019675 A1* | 1/2013 | Ban | G01F 1/6842 73/202 |
| 2013/0139584 A1* | 6/2013 | Qasimi | G01F 1/6842 29/592.1 |
| 2013/0205892 A1* | 8/2013 | Ueda | G01F 1/6842 73/202 |
| 2015/0247774 A1 | 9/2015 | Wagner et al. | |
| 2016/0161314 A1* | 6/2016 | Hunziker | H01L 24/49 438/55 |
| 2016/0223379 A1* | 8/2016 | Cook | G01F 15/006 |
| 2018/0070158 A1 | 3/2018 | Watson et al. | |
| 2018/0172493 A1* | 6/2018 | Speldrich | G01F 15/00 |
| 2018/0313709 A1 | 11/2018 | Chiou | |
| 2021/0116280 A1* | 4/2021 | Ali | G01F 1/696 |
| 2021/0116281 A1* | 4/2021 | Udrea | G01F 1/7084 |

FOREIGN PATENT DOCUMENTS

| | | | | |
|---|---|---|---|---|
| DE | 102012216511 A1 | * | 4/2014 | G01F 1/6842 |
| DE | 112013002999 B4 | * | 11/2021 | G01F 1/684 |
| EP | 2889587 A2 | | 7/2015 | |
| EP | 2069726 B1 | * | 7/2018 | G01F 1/6842 |
| IN | 106461480 A | | 2/2017 | |
| JP | 5425021 B2 | | 2/2014 | |

OTHER PUBLICATIONS

English Translation of CN Office Action Mailed on Jun. 8, 2022 for CN Application No. 202210169625.
European Search Report and Search Opinion received for EP Application No. 22156355.4, mailed on Oct. 17, 2022, 11 pages.
Partial European Search Report received for EP Application No. 22156355.4, mailed on Jul. 12, 2022, 7 pages.

* cited by examiner

FLOW SENSING DEVICE

BACKGROUND

Flow sensing devices may be used to measure a flow rate and/or quantity of a moving liquid or gas and may be implemented in various applications. For example, a flow sensing device may be a part of a system for measuring and/or controlling the dosing of liquid or gas.

Such flow sensing devices are plagued by technical challenges and limitations. Through applied effort, ingenuity, and innovation, many of these identified problems have been solved by developing solutions that are included in embodiments of the present disclosure, many examples of which are described in detail herein.

BRIEF SUMMARY

In accordance with various examples of the present disclosure, an example flow sensing device may be provided.

The example flow sensing device may comprise a housing, a sensing element disposed at least partially within the housing, and a plurality of channels disposed within the housing defining a flow path configured to convey a flowing media through the flow sensing device, wherein the flow path is disposed proximate the sensing element such that at least a portion of the flowing media makes direct contact with the sensing element.

In accordance with various examples of the present disclosure, a modular flow sensing assembly is provided. The modular flow sensing assembly may comprise: a first component comprising a flow sensing device and first processing circuitry; and a second component comprising second processing circuitry, wherein the first component and the second component are configured to form an electronic connection when mated.

In accordance with various examples of the present disclosure, a method for detecting a bubble in a flow path of a flow sensing assembly by a heating control circuit is provided. The method may comprise: controlling a thermal output of a heating element to maintain a predetermined temperature; monitoring a heating element output; and identifying the bubble based at least in part one or more characteristics of the heating element output.

The foregoing illustrative summary, as well as other exemplary objectives and/or advantages of the disclosure, and the manner in which the same may be accomplished, may be further explained in the following detailed description and its accompanying drawings.

BRIEF DESCRIPTION OF THE DRAWINGS

The description of the illustrative examples may be read in conjunction with the accompanying figures. It will be appreciated that, for simplicity and clarity of illustration, components and elements illustrated in the figures have not necessarily been drawn to scale, unless described otherwise. For example, the dimensions of some of the components or elements may be exaggerated relative to other components or elements, unless described otherwise. Examples incorporating teachings of the present disclosure are shown and described with respect to the figures presented herein, in which.

DETAILED DESCRIPTION OF THE INVENTION

Figure 1:
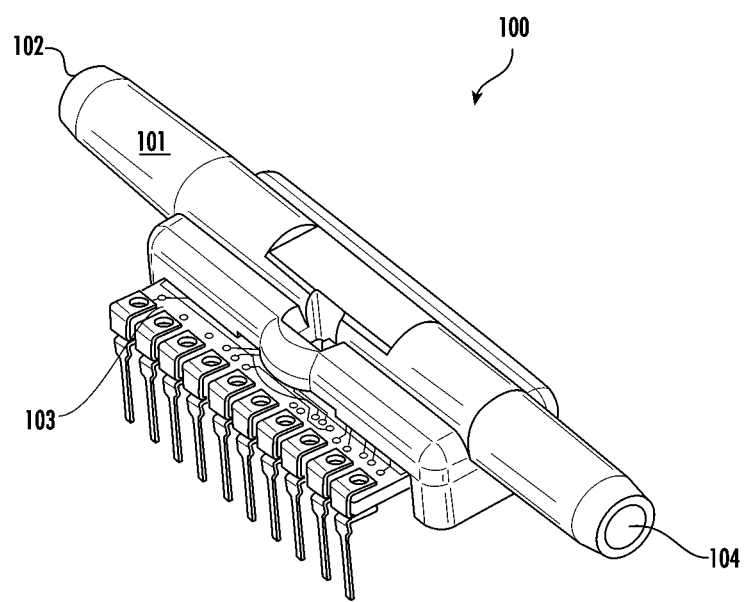
FIG. 1 illustrates a perspective view of an example flow sensing device, in accordance with examples of the present disclosure.

Some examples of the present disclosure will now be described more fully hereinafter with reference to the accompanying drawings, in which some, but not all examples of the disclosure are shown. Indeed, these disclosures may be embodied in many different forms and should not be construed as limited to the examples set forth herein;

rather, these examples are provided so that this disclosure will satisfy applicable legal requirements. Like numbers refer to like elements throughout.

The phrases "in one example," "according to one example," "in some examples," and the like generally mean that the particular feature, structure, or characteristic following the phrase may be included in at least one example of the present disclosure and may be included in more than one example of the present disclosure (importantly, such phrases do not necessarily refer to the same example).

If the specification states a component or feature "may," "can," "could," "should," "would," "preferably," "possibly," "typically," "optionally," "for example," "as an example," "in some examples," "often," or "might" (or other such language) be included or have a characteristic, that specific component or feature is not required to be included or to have the characteristic. Such component or feature may be optionally included in some examples, or it may be excluded.

The word "example" or "exemplary" is used herein to mean "serving as an example, instance, or illustration." Any implementation described herein as "example" or "exemplary" is not necessarily to be construed as preferred or advantageous over other implementations.

The term "electronically coupled," "electronically coupling," "electronically couple," "in communication with," "in electronic communication with," or "connected" in the present disclosure refers to two or more elements or components being connected through wired means and/or wireless means, such that signals, electrical voltage/current, data and/or information may be transmitted to and/or received from these elements or components.

The term "component" may refer to an article, a device, or an apparatus that may comprise one or more surfaces, portions, layers and/or elements. For example, an example component may comprise one or more substrates that may provide underlying layer(s) for the component, and may comprise one or more elements that may form part of and/or are disposed on top of the substrate. In the present disclosure, the term "element" may refer to an article, a device, or an apparatus that may provide one or more functionalities.

The term "flow sensing device" refers to an apparatus that may detect, measure, and/or identify flow rate(s) (including, but not limited to, linear flow velocity, nonlinear flow velocity, mass flow rate, and/or volumetric flow rate) of a flowing media or medium. In the present disclosure, the term "flowing media" refers to a substance (such as, but not limited to, liquid substance and/or gaseous substance).

The term "flow path" may refer to a passageway through which a flowing media may flow, traverse or be conveyed. As will be described in detail further herein, an example flow path of the present disclosure may be defined/formed by and/or comprise a plurality of channels. An example channel may define a plurality of sidewalls. In various examples of the present disclosure, example dimensions of example cross sections of example flow channels may be in the microns to hundreds of microns in height and tens of microns to hundreds of microns in width. In various examples of the present disclosure, example flow channels may be greater than one hundred microns in length. In some examples, various applications of present disclosure may require laminar flow, which may be characterized by particles of the flowing media following smooth path(s) in the flow channel with little or no mixing (i.e. high momentum diffusion and low momentum convection). In contrast, turbulent flow may be characterized by particles of the flowing media undergo irregular fluctuations, or mixing. In some examples, a laminar flow for the flow sensing device may be achieved based on the flow rate of the flowing media. As described herein, examples of the present disclosure may be implemented in an infusion pump, where the flow rate may be less than a flow rate threshold (for example, between 0.02 milliliters per hour (mL/hr) and 0.5 mL/hr). As such, in some examples, turbulent flow may be avoided by receiving a flowing media that has a flow rate below a flow rate threshold to retain the flowing media as laminar flow.

Flow sensing devices may be utilized in a variety of applications including micropipetting, high-performance liquid chromatography (HPLC) applications, drug delivery, and/or the like. For example, an example flow sensing device may be implemented in an invasive or non-invasive drug delivery system to detect, measure, and/or identify a flow rate of a flowing media associated with the invasive or non-invasive drug delivery system. In such an example, an infusion pump may be implemented to deliver substance(s) (such as, but not limited to, fluids, medications and/or nutrients) into a patient's body in an invasive drug delivery system. The substance(s) may need to be delivered in controlled amounts. As such, an example flow sensing device may be implemented in the infusion pump to detect, measure, and/or identify the flow rate of substance(s) that may be delivered to the patient.

In various examples, the flow rate of a flowing media may need to be precisely measured. Continuing from the infusion pump example above, the flow rate of the substance(s) may need to be delivered at a low rate based on the condition of the patient and/or the treatment for the patient. For example, the substance(s) may need to be delivered at less than 5 milliliters per hour. If the flow rate is not precisely measured, a patient may be over-dosed or under-dosed, which may result in injuries, casualties, and/or deaths. For example, in 2019, there were at least 21 deaths of patients in the United States that were known to be caused at least partially by over infusion of drugs in invasive drug delivery systems, which incurred at least seven million dollars cost.

Existing flow sensing devices are not capable of directly measuring a flow rate of a substance, for example, requiring measurement through or within a tube wall. Additionally, existing technology, such as ultrasonic technology, may be too expensive and complex to implement in such systems and have failed to receive wide adaptation and are highly inaccurate (e.g., high-pressure drops during operations may result in false or incorrect readings).

Using the systems, apparatuses and techniques disclosed herein, flow sensing devices configured for use in both low flow applications, high flow applications and combinations thereof are provided. The example flow sensing devices are capable of measuring a wide range of media flow rates over several orders of magnitude with increased accuracy. Additionally, the example flow sensing devices may reduce or eliminate unwanted high-pressure drops. As such, some examples of the present disclosure may, for example but not limited to, improve performance, sensitivity, accuracy, and/or drift of a flow sensing device, and/or may, in some examples, enable measurement of a flow rate in an infusion pump of an invasive drug delivery system.

To address challenges and limitations associated with measuring flow rates, various examples of the present disclosure may be provided. For example, various examples of the present disclosure may provide example flow sensing devices, apparatuses, methods and systems.

In various embodiments, the present disclosure may provide a flow sensing device. The example flow sensing device may comprise a housing, a sensing element disposed at least partially within the housing, and a plurality of channels disposed within the housing defining a flow path configured to convey a flowing media through the flow sensing device, wherein the flow path is disposed proximate the sensing element such that at least a portion of the flowing media makes direct contact with the sensing element.

Referring now to FIG. 1, a schematic diagram depicting a perspective view of an example flow sensing device 100 in accordance with various embodiments of the present disclosure is provided. As depicted in FIG. 1, the flow sensing device 100 comprises a housing 101 and a printed circuit board assembly (PCBA) 103.

As depicted in FIG. 1, the housing 101 of the example flow sensing device 100 may be or comprise a tubular shaped member configured to convey a flowing media from an inlet 102 of the flow sensing device 100 to an outlet 104 of the flow sensing device 100. In various embodiments, the flow sensing device 100 may form part of and/or be connected to an external flow channel (e.g., via a first tube connected to the inlet 102 and a second tube connected to the outlet 104) such that a flowing media can be conveyed therethrough. In various embodiments, the inlet 102 and the outlet 104 may define or comprise slide-on fittings, luer-lock, Swage-Lock, and/or the like. In various embodiments, the example housing 101 may be or comprise plastic, biodegradable materials, poly(methyl methacrylate) (PMMA), cyclic olefine copolymers, polycarbonate, polystyrene, polyether ether ketone (PEEK), polytetrafluoroethylene (PTFE), liquid-crystal polymers (LCPs), polyetherimide (PEI), epoxy, PerFluoroAlkoxy (PFA), fluorinated ethylene propylene (FEP), combinations thereof, and/or the like.

As noted above, the example flow sensing device 100 comprises a PCBA 103. In various examples, a surface of the example housing 101 may be disposed adjacent a surface of the PCBA 103. For example, as depicted in FIG. 1, a bottom surface of the housing 101 of the flow sensing device 100 may be disposed adjacent and/or attached to a top surface of the PCBA 103. In various embodiments, the PCBA 103 may be in electronic communication with one or more elements of the flow sensing device 100. By way of example, the example PCBA 103 may be in electronic communication with a sensing element (e.g., sense die, transducer and/or the like) of the flow sensing device 100. The example PCBA 103 may comprise an FR4. In various embodiments, the example PCBA 103 may comprise epoxy, ceramic, alumina, LCPs, and/or the like.

In various examples, the PCBA 103 may be electrically connected to an example sensing element (e.g., sense die) using various techniques. For example, wire bonds, bump bonds or the like may be utilized to electrically connect the example sensor to the PCBA 103. The example PCBA 103 may comprise a thick film printed ceramic board, a laminate and/or other material. As depicted in FIG. 1, the example PCBA 103 comprises one or more electronic components thereon and/or pads for connecting to other electronic components of the flow sensing device 100 and/or other apparatuses. In some examples, the PCBA 103 may include an application specific integrated circuit (ASIC) that may be attached to a surface of the PCBA 103, such as an ASIC electrically coupled to the PCBA 103 via wire bonds, bump bonds, electrical terminals, and/or any other suitable electrical connections. Additionally or alternatively, the example PCBA 103 may include one or more conductive pads for engaging circuitry and/or electronic components in communication with a remote processor or the like.

While the description above provides an example flow sensing device 100, it is noted that the scope of the present disclosure is not limited to the description above. In some examples, an example flow sensing device 100 may in accordance with the present disclosure may be in other forms. In some examples, an example flow sensing device 100 may comprise one or more additional and/or alternative elements, and/or may be structured/positioned differently than that illustrated in FIG. 1.

Figure 2:
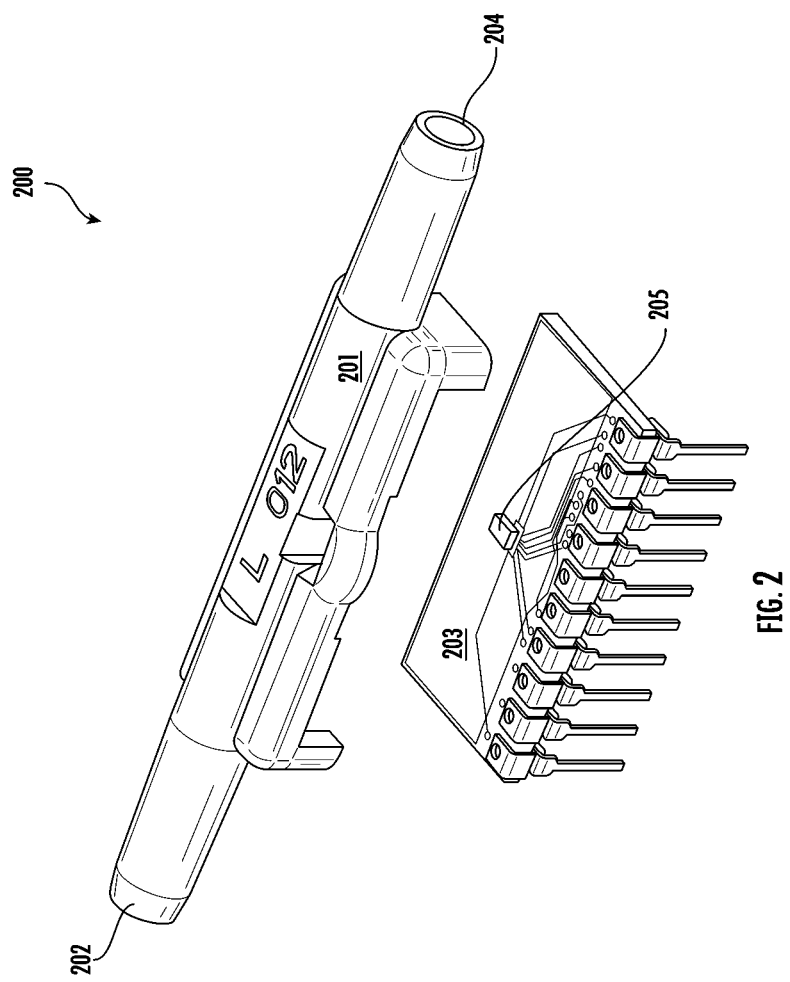
FIG. 2 illustrates an exploded perspective view of an example flow sensing device, in accordance with examples of the present disclosure.

Referring now to FIG. 2, a schematic diagram depicting an exploded view of an example flow sensing device 200 in accordance with various embodiments of the present disclosure is provided. The example flow sensing device 200 may be similar to the flow sensing device 100 described above in connection with FIG. 1. As depicted, the example flow sensing device 200 comprises a housing 201, a PCBA 203 and a sensing element 205.

As depicted in FIG. 2, the housing 201 of the example flow sensing device 200 may be or comprise a tubular shaped member configured to convey a flowing media from an inlet 202 of the flow sensing device 200 to an outlet 204 of the flow sensing device 200. In various embodiments, the flow sensing device 200 may form part of and/or be connected to an external flow channel (e.g., via a first tube connected to the inlet 202 and a second tube connected to the outlet 204) such that a flowing media can be conveyed therethrough. In various examples, a surface of the example housing 201 may be configured to be disposed/positioned adjacent a surface of the PCBA 203. For example, as depicted in FIG. 2, a bottom surface of the housing 201 of the flow sensing device 100 may be configured to be disposed adjacent and/or attached to a top surface of the PCBA 203.

As noted above, as depicted in FIG. 2, the example flow sensing device 200 comprises a sensing element 205. In some examples, the sensing element 205 may comprise a microelectromechanical system (MEMS) die. The example MEMS die may comprise one or more other circuitries, including, but not limited to, additional temperature sensing circuitry, communication circuitry (for example, near field communication (NFC) circuitry), and/or power control circuitry, such that the MEMS die may be integrated a control system (for example, a control system for an infusion pump). In some embodiments, the one or more circuitries may be part of the flow sensing device 200 and/or distinct from the example sensing element 205 (e.g., disposed adjacent the MEMS die). For example, the example MEMS die may be incorporated into an application-specific integrated circuit (ASIC) and may be external to the flow sensing device 200. The sensing element 205 may be in electronic communication with the PCBA 203. In various examples, the sensing element 205 may be electrically connected to the PCBA 203 using various techniques. For example, wire bonds, bump bonds or the like may be utilized to electrically connect the sensing element 205 to the PCBA 203.

In various examples, the PCBA 203 may comprise one or more processing electronics and/or compensation circuitry (e.g., which may or may not include an ASIC). Such processing electronics may be electrically connected to terminals of the sensing element 205, an ASIC (if present), and/or electrical terminals to process electrical signals from the example the sensing element 205 and/or to transfer outputs from the example the sensing element 205 to electronic components of one or more apparatuses used in conjunction with the flow sensing device 100. In some instances, the PCBA 203 may include circuitry that may be configured to format one or more output signals provided by the example the sensing element 205 into a particular output format. For example, circuitry of the PCBA 203 may be configured to format the output signal provided by the example the sensing element 205 into a ratio-metric output format, a current format, a digital output format and/or any other suitable format. In some cases, the circuitry of the PCBA 203 may be configured to provide an output to one or more electrical terminals facilitating electrical connections with electronic components of one or more apparatuses used in conjunction with the flow sensing device 200.

While the description above provides an example flow sensing device 200, it is noted that the scope of the present disclosure is not limited to the description above. In some examples, an example flow sensing device 200 may in accordance with the present disclosure may be in other forms. In some examples, an example flow sensing device 200 may comprise one or more additional and/or alternative elements, and/or may be structured/positioned differently than that illustrated in FIG. 2.

Figure 3:
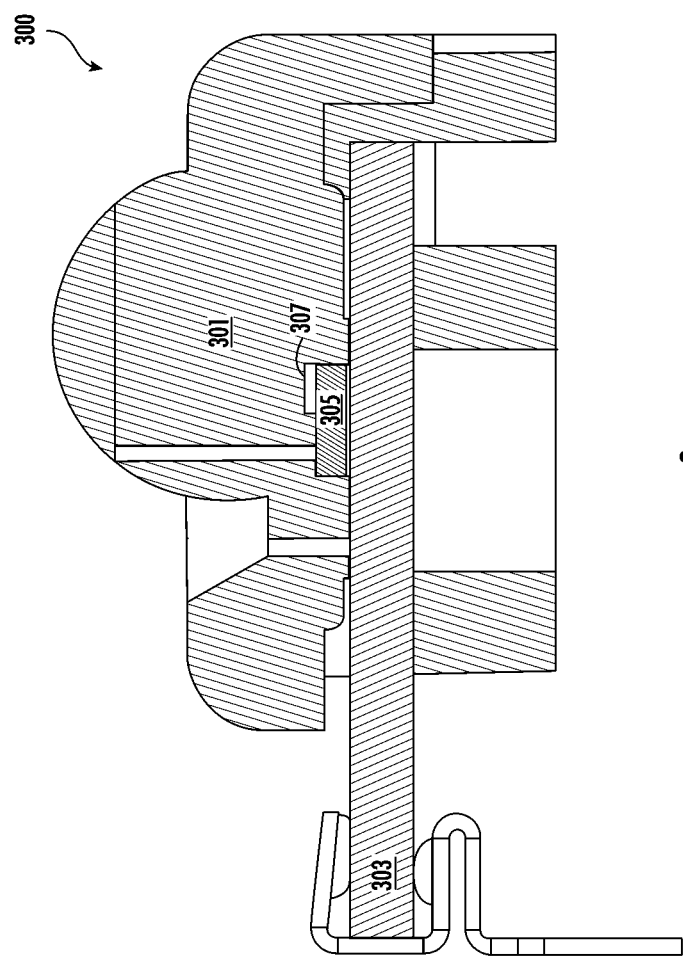
FIG. 3 illustrates a cross-sectional view of an example flow sensing device, in accordance with examples of the present disclosure.

Referring now to FIG. 3, a schematic diagram illustrating a cross sectional view of an example flow sensing device 300 in accordance with various embodiments of the present disclosure is provided. The example flow sensing device 300 may be utilized to determine low flow rate within a range (e.g., a low flow rate between about 1 μL/hour and about 10,000 μL/hour) associated with a flowing media. The example flow sensing device 300 may be similar to the flow sensing device 100 described above in connection with FIG. 1. As depicted, the example flow sensing device 300 comprises a housing 301. In various examples, as depicted, the housing defines an internal flow path 307 comprising one or more channels (e.g., a plurality of interconnected channels), a PCBA 303 and a sensing element 305.

As depicted in FIG. 3, the housing 301 of the example flow sensing device 300 may be or comprise a tubular shaped member configured to convey a flowing media from an inlet of the flow sensing device 300 to an outlet of the flow sensing device 300. As depicted in FIG. 3, the housing 301 of the flow sensing device 300 may comprise/define an internal flow path 307. In various embodiments, the example internal flow path 307 may comprise one or more channels. In various examples, the one or more channels may be or comprise a plurality of interconnected channels. As depicted, the internal flow path/channel(s) may be disposed adjacent (e.g., near, close to, and/or the like) the sensing element 305 of the flow sensing device 300. In various examples, the internal flow path/channel(s) may be disposed adjacent the sensing element 305 such that at least a portion of the flowing media makes direct contact with the sensing element 305. Said differently, at least a surface of the sensing element 305 may define a portion of the internal flow path of the example flow sensing device 300. In some examples, the internal flow path/channel(s) may define an angled geometry in order to direct (e.g., laminarize) the flowing media passing therethrough. In various embodiments, the flow sensing device 300 may form part of and/or be connected to an external flow channel such that a flowing media can be conveyed therethrough. As depicted in FIG. 3, the example internal flow path 307 comprises a channel disposed adjacent (e.g., above) the sensing element 305. In some examples, as shown, a top surface of the example sensing element 305 forms a portion of the internal flow path 307 such that at least a portion of the flowing media makes direct contact with the sensing element 305.

As noted above, the flow sensing device 300 comprises a PCBA 303. In various examples, a surface of the example housing 301 may be disposed/positioned adjacent a surface of the PCBA 303. For example, as depicted in FIG. 3, a bottom surface of the housing 301 of the flow sensing device 300 is disposed adjacent a top surface of the PCBA 303.

As noted above, and as depicted in FIG. 3, the example flow sensing device 300 comprises a sensing element 305. The sensing element 305 may be in electronic communication with the PCBA 303. In various examples, the sensing element 305 may be electrically connected to the PCBA 303 using various techniques (e.g., wire bonds, bump bonds or the like) to electrically connect the sensing element 305 to the PCBA 303.

In various embodiments, at least a surface of the sensing element 305 may be disposed adjacent a surface of the PCBA 303. For example, as depicted, a bottom surface of the sensing element 305 may be disposed adjacent (e.g., attached to) a top surface of the PCBA 303. Additionally, in various examples, at least a portion of the sensing element 305 may be disposed at least partially within the housing 301 of the example flow sensing device 300. For example, as shown, the sensing element 305 may be disposed centrally within the housing 301 and adjacent a bottom surface of the housing 301 of the flow sensing device 300.

In various examples, the PCBA 303 may comprise one or more processing electronics and/or compensation circuitry (e.g., which may or may not include an ASIC). Such processing electronics may be electrically connected to terminals of the sensing element 305, an ASIC (if present), and/or electrical terminals to process electrical signals from the example the sensing element 305 and/or to transfer outputs from the example the sensing element 305 to electronic components of one or more apparatuses used in conjunction with the flow sensing device 300.\

While the description above provides an example flow sensing device 300, it is noted that the scope of the present disclosure is not limited to the description above. In some examples, an example flow sensing device 300 may in accordance with the present disclosure may be in other forms. In some examples, an example flow sensing device 300 may comprise one or more additional and/or alternative elements, and/or may be structured/positioned differently than that illustrated in FIG. 3.

Figure 4:
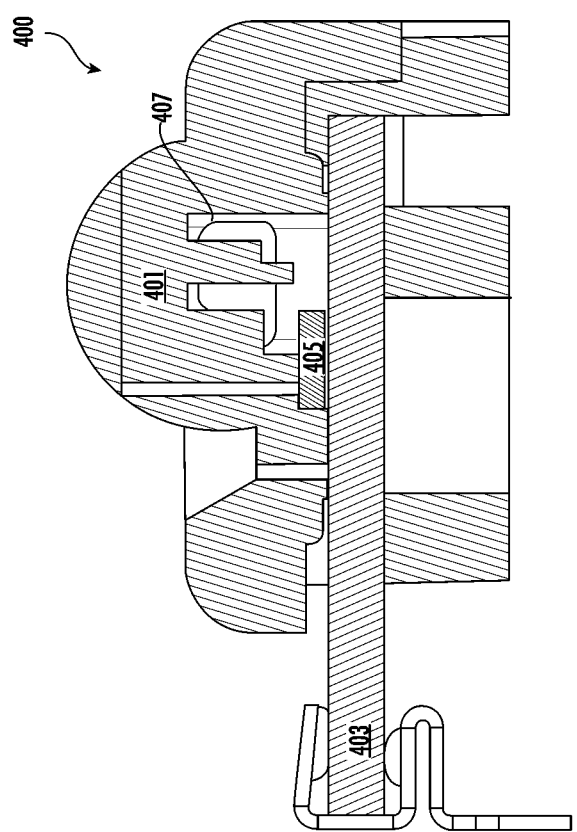
FIG. 4 illustrates a cross-sectional view of an example flow sensing device, in accordance with examples of the present disclosure.

Referring now to FIG. 4, a schematic diagram illustrating a cross sectional view of at least a portion of an example flow sensing device 400 in accordance with various embodiments of the present disclosure is provided. The example flow sensing device 400 may be utilized to determine a high flow rate (e.g., a high flow rate between about 1 mL/hr and about 1000 mL/hr) associated with a flowing media. The example flow sensing device 400 may be similar to the flow sensing device 100 described above in connection with FIG. 1. As depicted, the example flow sensing device 400 comprises a housing 401 defining an internal flow path 407 comprising one or more channels, a PCBA 403 and a sensing element 405.

As depicted in FIG. 4, the housing 401 of the example flow sensing device 400 may be or comprise a tubular shaped member configured to convey a flowing media from an inlet of the flow sensing device 400 to an outlet of the flow sensing device 400. As depicted, the housing 401 of the flow sensing device 400 may define the internal flow path 407 comprising one or more channels. In various examples, the internal flow path/channel(s) may be or comprise a plurality of interconnected channels. In various examples, the internal flow path 407 may be disposed adjacent (e.g., near, close to, and/or the like) the sensing element 405 of the flow sensing device 400. In various examples, the internal flow path/channel(s) may be disposed adjacent the sensing element 405 such that at least a portion of the flowing media makes direct contact with the sensing element 405. In some examples, the internal flow path/channel(s) may define an angled geometry (i.e., a non-planar geometry) in order to direct (e.g., laminarize) the flowing media passing therethrough. In various embodiments, the flow sensing device 400 may form part of and/or be connected to an external flow channel such that a flowing media can be conveyed therethrough. As depicted in FIG. 4, the example internal flow path 407 comprises a channel disposed adjacent the sensing element 405. As shown, at least a surface of the sensing element 405 may form a portion of the internal flow path 407 such that at least a portion of the flowing media makes direct contact with the sensing element 405. In various examples, as depicted in FIG. 4, in order to satisfy various low pressure drop specifications and requirements, the example internal flow path 407 for the example high flow rate flow sensing device 400 may comprise a larger cross-section than that of an example low flow rate flow sensing device (e.g., flow sensing device 300 described above in connection with FIG. 3).

As noted above, the flow sensing device 400 comprises a PCBA 403. In various examples, a surface of the example housing 401 may be disposed/positioned adjacent a surface of the PCBA 403. For example, as depicted in FIG. 4, a bottom surface of the housing 401 of the flow sensing device 400 is disposed adjacent a top surface of the PCBA 403.

As noted above, and as depicted in FIG. 4, the example flow sensing device 400 comprises a sensing element 405. The sensing element 405 may be in electronic communication with the PCBA 403. In various examples, the sensing element 405 may be electrically connected to the PCBA 403 using various techniques (e.g., wire bonds, bump bonds or the like) to electrically connect the sensing element 405 to the PCBA 403.

In various embodiments, at least a surface of the sensing element 405 may be disposed adjacent a surface of the PCBA 403. For example, as depicted, a bottom surface of the sensing element 405 may be disposed adjacent (e.g., attached to) a top surface of the PCBA 403. Additionally, in various examples, at least a portion of the sensing element 405 may be disposed at least partially within the housing 401 of the example flow sensing device 400. For example, as shown, the sensing element 405 may be disposed centrally within the housing 401 and adjacent a bottom surface of the housing 401 of the flow sensing device 400.

In various examples, the PCBA 403 may comprise one or more processing electronics and/or compensation circuitry (e.g., which may or may not include an ASIC). Such processing electronics may be electrically connected to terminals of the sensing element 405, an ASIC (if present), and/or electrical terminals to process electrical signals from the example the sensing element 405 and/or to transfer outputs from the example the sensing element 405 to electronic components of one or more apparatuses used in conjunction with the flow sensing device 400.

While the description above provides an example flow sensing device 400, it is noted that the scope of the present disclosure is not limited to the description above. In some examples, an example flow sensing device 400 may in accordance with the present disclosure may be in other forms. In some examples, an example flow sensing device 400 may comprise one or more additional and/or alternative elements, and/or may be structured/positioned differently than that illustrated in FIG. 4.

Figure 5:
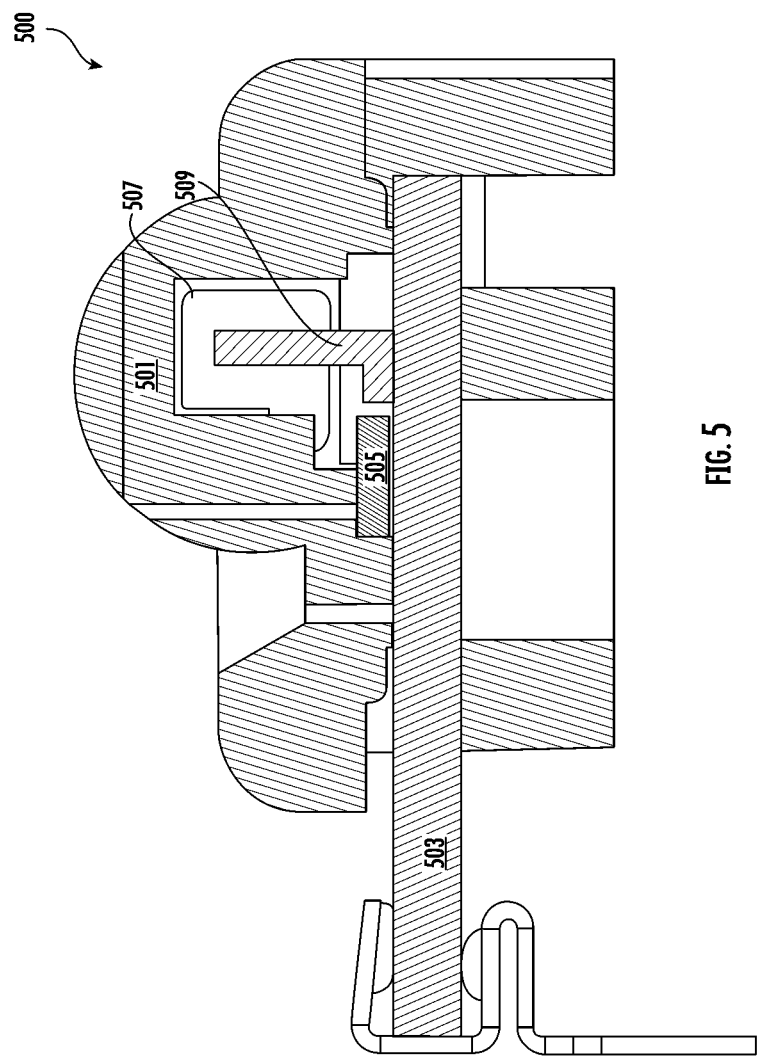
FIG. 5 illustrates a cross-sectional view of an example flow sensing device, in accordance with examples of the present disclosure.

Referring now to FIG. 5, a schematic diagram illustrating a cross sectional view of at least a portion of an example flow sensing device 500 in accordance with various embodiments of the present disclosure is provided. The example flow sensing device 500 may be utilized to determine a high flow rate (e.g., a high flow rate between about 1 mL/hr and about 1000 mL/hr) associated with a flowing media. The example flow sensing device 500 may be similar to the flow sensing device 100 described above in connection with FIG. 1. As depicted, the example flow sensing device 500 comprises a housing 501 defining an internal flow path 507 comprising one or more channels, a PCBA 503, a sensing element 505 and a shielding element 509. In various examples, the shielding element 509 may operate to direct a flowing media within the flow path/channel of the example flow sensing device 500 such that at least a portion of the flowing media makes contact with at least a surface of the example sensing element 505 and/or is diverted from at least another surface of the example sensing element 505. In various embodiment, the example shielding element 509 may comprise materials similar to example flow sensing device such as plastic, biodegradable materials, poly(methyl methacrylate) (PMMA), cyclic olefine copolymers, polycarbonate, polystyrene, polyether ether ketone (PEEK), polytetrafluoroethylene (PTFE), liquid-crystal polymers (LCPs), polyetherimide (PEI), epoxy, PerFluoroAlkoxy (PFA), fluorinated ethylene propylene (FEP), combinations thereof, and/or the like.

As depicted in FIG. 5, the housing 501 of the example flow sensing device 500 may be or comprise a tubular shaped member configured to convey a flowing media from an inlet of the flow sensing device 500 to an outlet of the flow sensing device 500. As depicted, the housing 501 of the flow sensing device 500 may define the internal flow path/channel(s). In various examples, the internal flow path 507 may be or comprise a plurality of interconnected channels. As depicted, the internal flow path/channel(s) may be disposed adjacent (e.g., near, close to, and/or the like) the sensing element 505 of the flow sensing device 500. In various examples, the internal flow path/channel(s) may be disposed adjacent the sensing element 505 such that at least a portion of the flowing media makes direct contact with the sensing element 505. In some examples, the internal flow path/channel(s) may define an angled geometry (e.g., non-planar geometry) in order to direct (e.g., laminarize) the flowing media passing therethrough. In various embodiments, the flow sensing device 500 may form part of and/or be connected to an external flow channel such that a flowing media can be conveyed therethrough. As depicted in FIG. 5, the example internal flow path 507 comprises a channel disposed adjacent the sensing element 505. As shown, at least a surface of the sensing element 505 may form a portion of the internal flow path 507 such that at least a portion of the flowing media makes direct contact with the sensing element 505.

As noted above, the flow sensing device 500 comprises a shielding element 509. The shielding element 509 may define at least a portion of the internal flow path 507 and/or one or more apertures within the flow sensing device 500. For example, as depicted, the shielding element 509 may be a distinct element defining at least a portion of the internal flow path 507 within the housing 501 of the flow sensing device 500. In various embodiments, the shielding element 509 may be configured to regulate (e.g., limit, channel, direct, and/or the like) an amount and/or flow of a flowing media making direct contact with the sensing element 505. The example shielding element 509 may operate to improve a flow characteristic (e.g., laminarize a flow) over at least a surface of the example sensing element 505. Additionally, in some examples, one or more surfaces of the example shielding element 509 may also operate to shield at least a portion or surface of the sensing element 505. In various examples, as depicted, the shielding element 509 may be disposed adjacent (e.g., near, close to and/or the like) the sensing element 505. For example, as depicted, at least a portion of the shielding element 509 may be in direct contact with at least a portion of the sensing element 505.

As noted above, the flow sensing device 500 comprises a PCBA 503. In various examples, a surface of the example housing 501 may be disposed/positioned adjacent a surface of the PCBA 503. For example, as depicted in FIG. 5, a bottom surface of the housing 501 of the flow sensing device 500 is disposed adjacent a top surface of the PCBA 503.

As noted above, and as depicted in FIG. 5, the example flow sensing device 500 comprises a sensing element 505. The sensing element 505 may be in electronic communication with the PCBA 503. In various examples, the sensing element 505 may be electrically connected to the PCBA 503 using various techniques (e.g., wire bonds, bump bonds or the like) to electrically connect the sensing element 505 to the PCBA 503.

In various embodiments, at least a surface of the sensing element 505 may be disposed adjacent a surface of the PCBA 503. For example, as depicted, a bottom surface of the sensing element 505 may be disposed adjacent (e.g., attached to) a top surface of the PCBA 503. Additionally, in various examples, at least a portion of the sensing element 505 may be disposed at least partially within the housing 501 of the example flow sensing device 500. For example, as shown, the sensing element 505 may be disposed centrally within the housing 501 and adjacent a bottom surface of the housing 501 of the flow sensing device 500.

In various examples, the PCBA 503 may comprise one or more processing electronics and/or compensation circuitry (e.g., which may or may not include an ASIC). Such processing electronics may be electrically connected to terminals of the sensing element 505, an ASIC (if present), and/or electrical terminals to process electrical signals from the example the sensing element 505 and/or to transfer outputs from the example the sensing element 505 to electronic components of one or more apparatuses used in conjunction with the flow sensing device 500.

While the description above provides an example flow sensing device 500, it is noted that the scope of the present disclosure is not limited to the description above. In some examples, an example flow sensing device 500 may in accordance with the present disclosure may be in other forms. In some examples, an example flow sensing device 500 may comprise one or more additional and/or alternative elements, and/or may be structured/positioned differently than that illustrated in FIG. 5.

Figure 6:
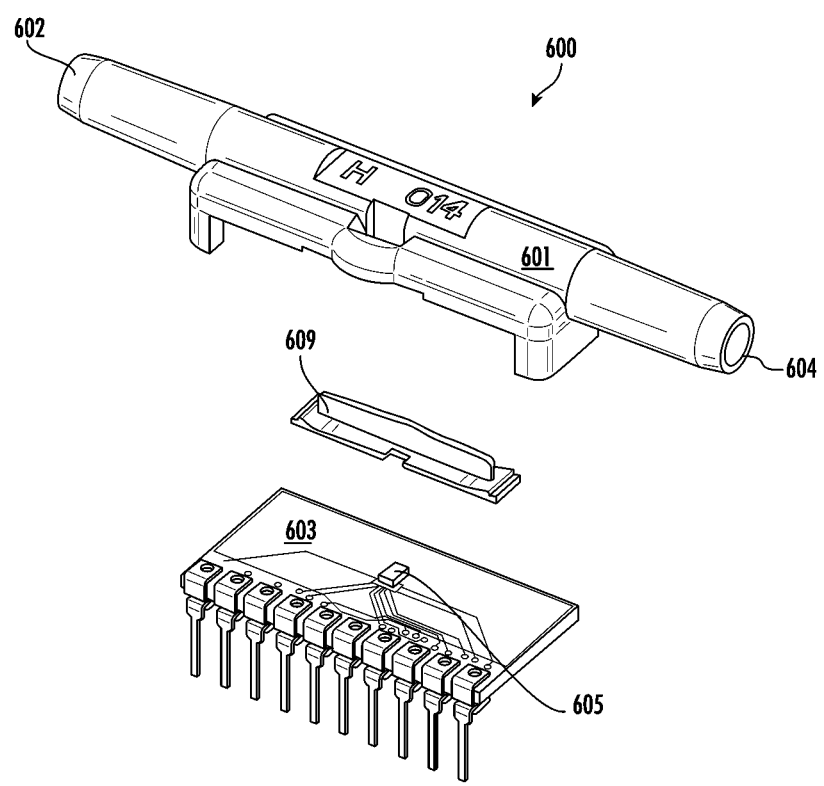
FIG. 6 illustrates an exploded perspective view of an example flow sensing device, in accordance with examples of the present disclosure.

Referring now to FIG. 6, a schematic diagram depicting an exploded view of an example flow sensing device 600 in accordance with various embodiments of the present disclosure is provided. The example flow sensing device 600 may be similar to the flow sensing device 500 described above in connection with FIG. 5. The example flow sensing device 600 may be utilized to determine a high flow rate (e.g., a high flow rate between about 1 mL/hr and about 1000 mL/hr) associated with a flowing media. As depicted, the example flow sensing device 600 comprises a housing 601 defining an internal flow path/channel(s), a PCBA 603, a sensing element 605 and a shielding element 609.

As depicted in FIG. 6, the housing 601 of the example flow sensing device 600 may be or comprise a tubular shaped member configured to convey a flowing media from an inlet 602 of the flow sensing device 600 to an outlet 604 of the flow sensing device 600. In various embodiments, the internal flow path/channel(s) of the flow sensing device 600 may be or comprise a plurality of interconnected channels. In some examples, the internal flow path/channel(s) may be disposed adjacent (e.g., near, close to, and/or the like) the sensing element 605 of the flow sensing device 600. In various examples, the internal flow path/channel(s) may be disposed adjacent the sensing element 605 such that at least a portion of a flowing media makes direct contact with the sensing element 605. In some examples, the internal flow path/channel(s) may define an angled geometry in order to direct (e.g., laminarize) the flowing media passing therethrough. In various embodiments, the flow sensing device 600 may form part of and/or be connected to an external flow channel such that a flowing media can be conveyed therethrough.

As noted above, the flow sensing device 600 comprises a shielding element 609. As depicted, in some examples, the shielding element 609 is a distinct element from the flow sensing device 600. In various embodiments, the shielding element 609 may define at least a portion of the internal flow path/channel(s) within the housing 601 of the flow sensing device 600. In various embodiments, the shielding element 609 may be configured to regulate (e.g., limit, channel, direct, laminarize, and/or the like) an amount and/or flow of a flowing media making direct contact with the sensing element 605. Additionally, in some examples, one or more surfaces of the example an internal flow path/channel(s) of the housing 601 and/or one or more surfaces of the example shielding element 609 may be utilized to shield at least a portion or surface of the sensing element 605. The shielding element 609 may be disposed at least partially between a surface of the housing 601 and a surface of the PCBA 603 and/or sensing element 605. In various examples, the shielding element 609 may be disposed adjacent (e.g., near, close to and/or the like) the sensing element 605. For example, as depicted, at least a portion of the shielding element 609 may be in direct contact with at least a portion of the sensing element 605.

As noted above, the flow sensing device 600 comprises a PCBA 603. In various examples, a surface of the example housing 601 may be disposed/positioned adjacent a surface of the PCBA 603.

As noted above, and as depicted in FIG. 6, the example flow sensing device 600 comprises a sensing element 605. The sensing element 605 may be in electronic communication with the PCBA 603. In various examples, the sensing element 605 may be electrically connected to the PCBA 603 using various techniques (e.g., wire bonds, bump bonds or the like) to electrically connect the sensing element 605 to the PCBA 603.

In various embodiments, at least a surface of the sensing element 605 may be disposed adjacent a surface of the PCBA 603. For example, as depicted, a bottom surface of the sensing element 605 may be disposed adjacent (e.g., attached to) a top surface of the PCBA 603. Additionally, in various examples, at least a portion of the sensing element 605 may be disposed at least partially within the housing 601 of the example flow sensing device 600. For example, the sensing element 605 may be disposed centrally within the housing 601 and adjacent a bottom surface of the housing 601 of the flow sensing device 600.

In various examples, the PCBA 603 may comprise one or more processing electronics and/or compensation circuitry (e.g., which may or may not include an ASIC). Such processing electronics may be electrically connected to terminals of the sensing element 605, an ASIC (if present), and/or electrical terminals to process electrical signals from the example the sensing element 605 and/or to transfer outputs from the example the sensing element 605 to electronic components of one or more apparatuses used in conjunction with the flow sensing device 600.

While the description above provides an example flow sensing device 600, it is noted that the scope of the present disclosure is not limited to the description above. In some examples, an example flow sensing device 600 may in accordance with the present disclosure may be in other forms. In some examples, an example flow sensing device 600 may comprise one or more additional and/or alternative elements, and/or may be structured/positioned differently than that illustrated in FIG. 6. For example, in some embodiments, the housing 601 of the flow sensing device 600 and the shielding element 609 may define a unitary body.

Figure 7:
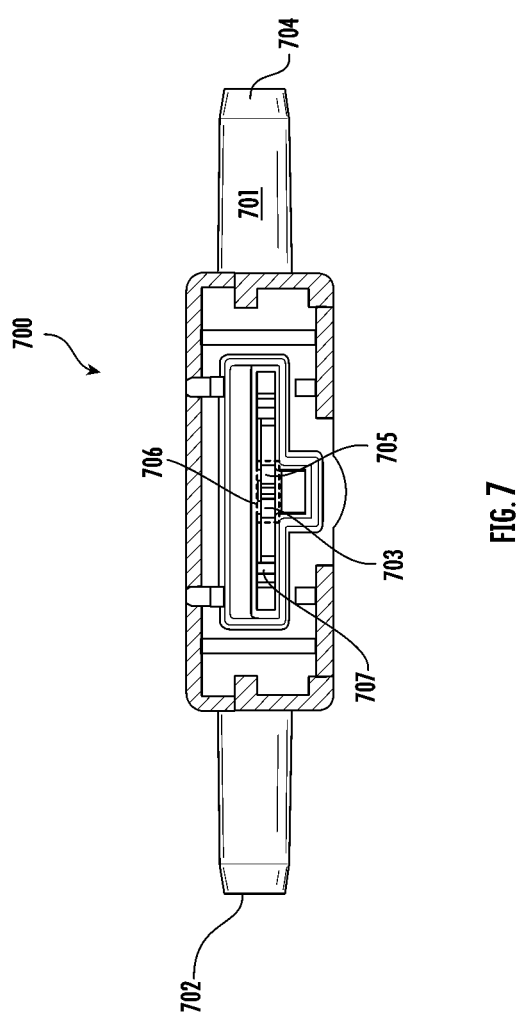
FIG. 7 illustrates a cross-sectional view of an example flow sensing device, in accordance with examples of the present disclosure.

Referring now to FIG. 7, a schematic diagram depicting a top cross-sectional view of an example flow sensing device 700 in accordance with various embodiments of the present disclosure is provided. The example flow sensing device 700 may be similar to the flow sensing device 700 described above in connection with FIG. 7. The example flow sensing device 700 may be utilized to determine a low flow rate (e.g., a low flow rate between about 1 µL/hour and about 10,000 µL/hour) associated with a flowing media. As depicted, the example flow sensing device 700 comprises a housing 701 defining an internal flow path 707 comprising one or more channels.

As depicted in FIG. 7, the housing 701 of the example flow sensing device 700 may be or comprise a tubular shaped member defining an internal flow path 707. In various embodiments, the example flow sensing device 700 is configured to convey a flowing media from an inlet 702 of the flow sensing device 700 to an outlet 704 of the flow sensing device 700.

In various embodiments, the internal flow path 707 of the flow sensing device 700 may be or comprise a plurality of interconnected channels. In some examples, at least one surface of the internal flow path 707 may be disposed adjacent (e.g., near, close to, and/or the like) an example sensing element of the flow sensing device 700. In various examples, the internal flow path 707/channel(s) of the flow sensing device 700 define an angled geometry configured to direct the flowing media passing therethrough. In various embodiments, the flow sensing device 700 may form part of and/or be connected to an external flow channel such that a flowing media can be conveyed therethrough. For example, as depicted in FIG. 7, at least a portion 706 of an example flow path 707/channel comprises at least an upstream portion 703 and a downstream portion 705. Accordingly, a flowing media may be channeled in an upward direction via the upstream portion 703 and in a downward direction via the downstream portion 705 as it is conveyed through the flow sensing device 700.

While the description above provides an example flow sensing device 700, it is noted that the scope of the present disclosure is not limited to the description above. In some examples, an example flow sensing device 700 may in accordance with the present disclosure may be in other forms. In some examples, an example flow sensing device 700 may comprise one or more additional and/or alternative elements, and/or may be structured/positioned differently than that illustrated in FIG. 7.

Figure 8:
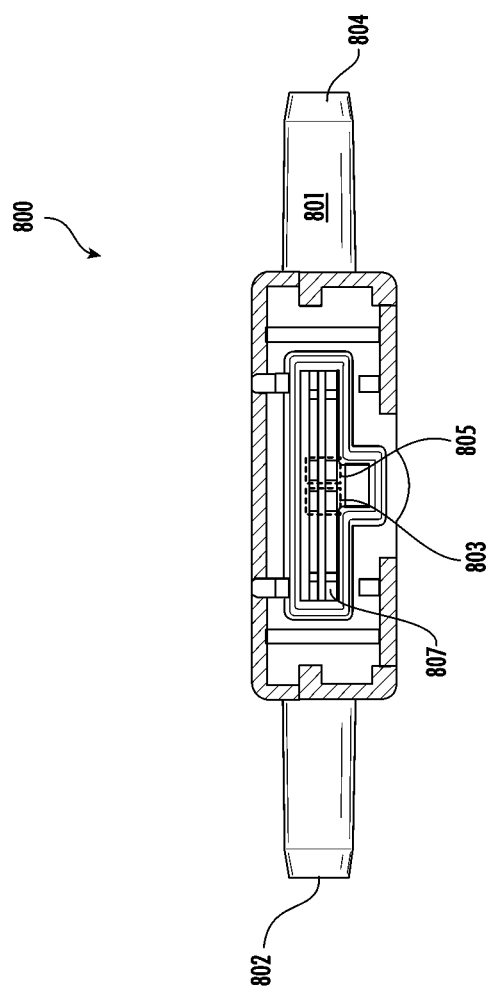
FIG. 8 illustrates a cross-sectional view of an example flow sensing device, in accordance with examples of the present disclosure.

Referring now to FIG. 8, a schematic diagram depicting a top cross-sectional view of an example flow sensing device 800 in accordance with various embodiments of the present disclosure is provided. The example flow sensing device 800 may be similar to the flow sensing device 400 described above in connection with FIG. 4. The example flow sensing device 800 may be utilized to determine a high flow rate (e.g., a high flow rate between about 1 mL/hr and about 1000 mL/hr) an amount and/or flow of a flowing media making direct contact with the sensing element 505.

As depicted in FIG. 8, the housing 801 of the example flow sensing device 800 may be or comprise a tubular shaped member defining an internal flow path 807 comprising one or more channels. In various embodiments, the example flow sensing device 800 is configured to convey a flowing media from an inlet 802 of the flow sensing device 800 to an outlet 804 of the flow sensing device 800.

In various embodiments, the internal flow path 807 of the flow sensing device 800 may be or comprise a plurality of interconnected channels. In some examples, at least one surface of the internal flow path 807 may be disposed adjacent (e.g., near, close to, and/or the like) an example sensing element of the flow sensing device 800. In various examples, the internal flow path 807/channel(s) of the flow sensing device 800 define an angled geometry configured to direct the flowing media passing therethrough. In various embodiments, the flow sensing device 800 may form part of and/or be connected to an external flow channel such that a flowing media can be conveyed therethrough. For example, as depicted in FIG. 8, at least a portion of the example internal flow path 807/channel comprises at least an upstream portion 803 and at least a downstream portion 805. Accordingly, a flowing media may be channeled in an upward direction via the upstream portion(s) 803 and in a downward direction via the downstream portion(s) 805 as it is conveyed through the flow sensing device 800. In some embodiments, at least a portion of the example channel may define a laminarizing fin which may operate to improve uniformity of flow velocity associated with a flowing media within the example internal flow path/channel(s) of the flow sensing device 800.

While the description above provides an example flow sensing device 800, it is noted that the scope of the present disclosure is not limited to the description above. In some examples, an example flow sensing device 800 may in accordance with the present disclosure may be in other forms. In some examples, an example flow sensing device 800 may comprise one or more additional and/or alternative elements, and/or may be structured/positioned differently than that illustrated in FIG. 8.

Figure 9:
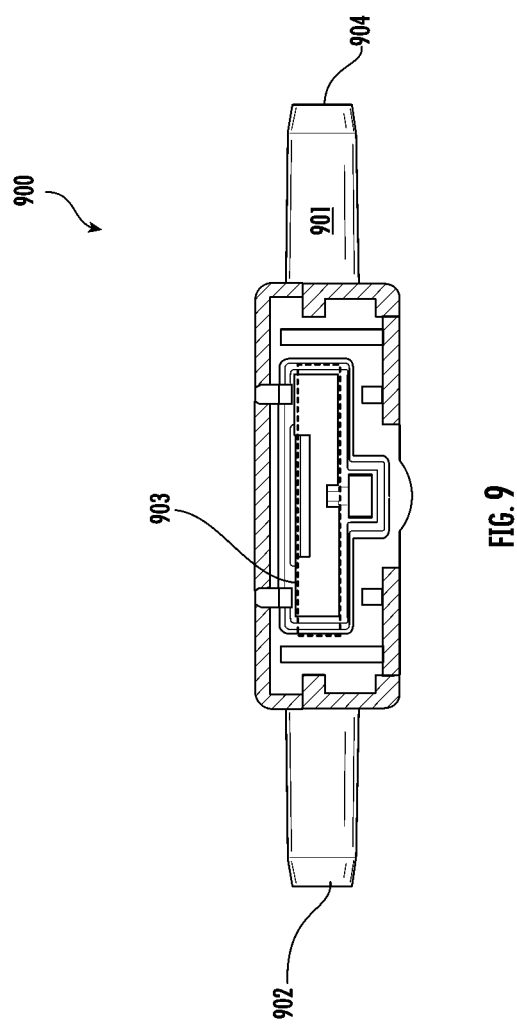
FIG. 9 illustrates a cross-sectional view of an example flow sensing device, in accordance with examples of the present disclosure.

Referring now to FIG. 9, a schematic diagram depicting a top cross-sectional view of an example flow sensing device 900 in accordance with various embodiments of the present disclosure is provided. The example flow sensing device 900 may be similar to the flow sensing device 500 described above in connection with FIG. 5. The example flow sensing device 900 may be utilized to determine a high flow rate (e.g., a high flow rate between about 1 mL/hr and about 1000 mL/hr) associated with a flowing media. As depicted, the example flow sensing device 900 comprises a housing 901 defining an internal flow path/channel(s) and a shielding element 903.

As depicted in FIG. 9, the housing 901 of the example flow sensing device 900 may be or comprise a tubular shaped member defining an internal flow path/channel(s). In various embodiments, the example flow sensing device 900 may be configured to convey a flowing media from an inlet 902 of the flow sensing device 900 to an outlet 904 of the flow sensing device 900. In some examples, the flow sensing device 900 comprises internal baffles disposed within an area proximate the inlet 902 and an area proximate the outlet 904 of the flow sensing device 900 to direct the flowing media through the flow sensing device 900.

In various embodiments, the internal flow path/channel(s) of the flow sensing device 900 may be or comprise a plurality of interconnected channels. In some examples, at least one surface of the least one internal flow path/channel(s) may be disposed adjacent (e.g., near, close to, and/or the like) an example sensing element of the flow sensing device 900. In various examples, at least a portion of the internal flow path/channel(s) of the flow sensing device 900 defines an angled geometry configured to direct the flowing media passing therethrough. In various embodiments, the flow sensing device 900 may form part of and/or be connected to an external flow channel such that a flowing media can be conveyed therethrough.

In some embodiments, as depicted in FIG. 9, the flow sensing device 900 comprises a shielding element 903 configured to direct at least a portion of a flowing media to make direct contact with a sensing element of the flow sensing device 900. In various embodiments, the shielding element 903 may define at least a portion of the internal flow path/channel(s) of the flow sensing device 900. For example, as depicted, the shielding element 903 may be a distinct element defining at least one channel within the housing 901 of the flow sensing device 900. In various embodiments, as depicted, the shielding element 903 may be or comprise a laminarizing fin. The example shielding element 903 (e.g. laminarizing fin) may operate to improve uniformity of flow velocity (e.g., over at least a surface of the sensing element) associated with a flowing media within the example an internal flow path/channel(s) of the flow sensing device 900. In various embodiments, the shielding element 903 may be configured to regulate (e.g., limit, channel, direct, and/or the like) an amount and/or flow of a flowing media making direct contact with the sensing element 505. Additionally, in some examples, one or more surfaces of the shielding element 903 may be in direct contact with at least a portion or surface of an example sensing element.

While the description above provides an example flow sensing device 900, it is noted that the scope of the present disclosure is not limited to the description above. In some examples, an example flow sensing device 900 may in accordance with the present disclosure may be in other forms. In some examples, an example flow sensing device 900 may comprise one or more additional and/or alternative elements, and/or may be structured/positioned differently than that illustrated in FIG. 9.

Figure 10:
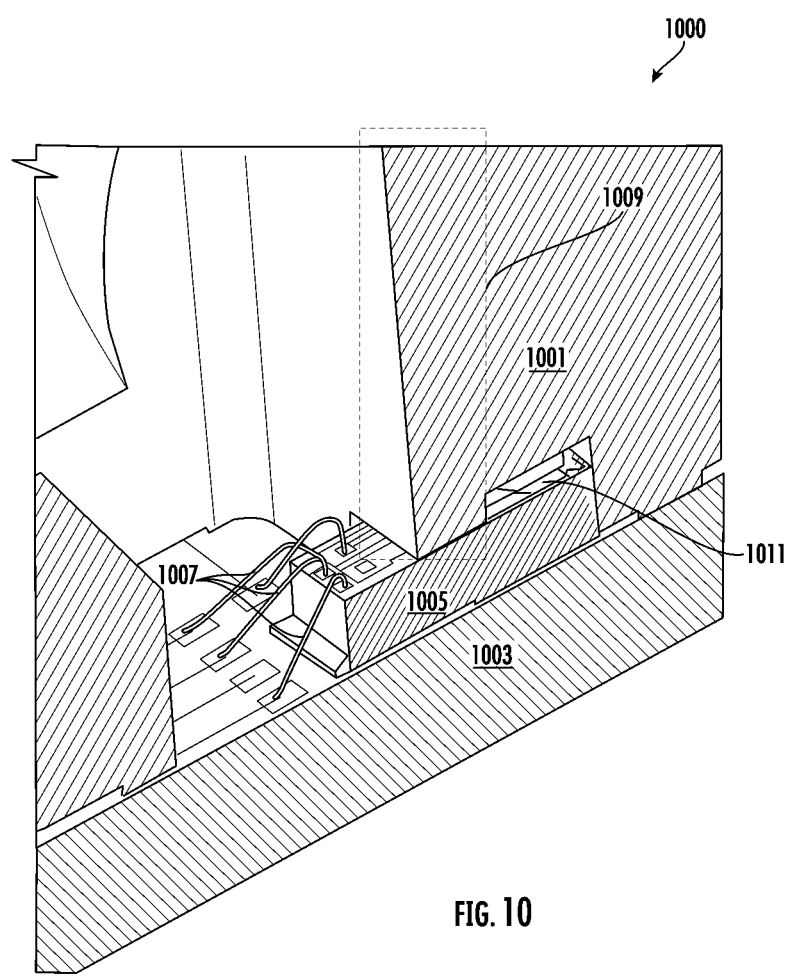
FIG. 10 illustrates a perspective view of an example flow sensing device, in accordance with examples of the present disclosure.

Referring now to FIG. 10, a schematic diagram depicting a perspective view of a portion of an example flow sensing device 1000 in accordance with various embodiments of the present disclosure is provided. The example flow sensing device 1000 may be similar to the flow sensing device 1000 described above in connection with FIG. 3. The example flow sensing device 1000 may be utilized to determine a low flow rate (e.g., low flow rates between about 1 μL/hour and about 10,000 μL/hour) associated with a flowing media. As depicted, the example flow sensing device 1000 comprises a housing 1001 defining an internal flow path/channel(s), a sensing element 1005 and a PCBA 1003.

As depicted in FIG. 10, the housing 101 of the example flow sensing device 1000 may be or comprise a tubular shaped member defining an internal flow path/channel(s). In various embodiments, the example flow sensing device 1000 may be configured to convey a flowing media therethrough.

In various embodiments, the internal flow path/channel(s) of the flow sensing device 1000 may be or comprise a plurality of interconnected channels. In various examples, the internal flow path/channel(s) of the flow sensing device 1000 defines an angled geometry configured to direct the flowing media passing therethrough. For example, the plurality of interconnected channels may operate to laminarize the flow of a flowing media thereby improving a signal quality detected by the sensing element 1005 and eliminating extraneous noise. In various examples, at least one surface of the least one internal flow path/channel(s) may be disposed adjacent (e.g., near, close to, and/or the like) the example sensing element 1005 of the flow sensing device 1000.

As noted above, the flow sensing device 1000 comprises a sensing element 1005. The sensing element 1005 may be in electronic communication with the PCBA 1003. In various examples, the sensing element 1005 may be electrically connected to the PCBA 1003 using various techniques (e.g., wire bonds, bump bonds or the like) to electrically connect the sensing element 1005 to the PCBA 1003. As depicted in FIG. 10, the sensing element 1005 may be electrically connected to the PCBA 1003 via a plurality of wire bonds 1007. In some examples, the sensing element 1005 may be or comprise a microelectromechanical systems (MEMS) sensor. The example MEMS sensor may be suitable for a disposable component of an example flow sensing device, as discussed elsewhere herein. In various embodiments, the example MEMS sensor may be coated with an MEMS passivation material (e.g., silicon nitride). Accordingly, the passivation material may serve as the only barrier between the example MEMS sensor and a flowing media such that a signal quality detected by the example MEMS sensor is maximized.

In various embodiments, the flow sensing device 1000 may form part of and/or be connected to an external flow channel such that a flowing media can be conveyed therethrough. As depicted in FIG. 10, at least a surface of the housing 1001 (e.g., a surface of an internal flow path/channel(s)) may be at least partially disposed adjacent (e.g., near, close to, or the like) the sensing element 1005 of the flow sensing device 1000 such that at least a portion (e.g., sample) of the flowing media makes direct contact with the sensing element 1005. As depicted, the flowing media may be conveyed via an aperture 1011 disposed between a bottom surface of the housing 1001 and at least a portion of a top surface of the sensing element 1005. In some examples, the internal flow path/channel(s) may define an angled geometry in order to direct the flowing media passing therethrough. In some examples, as depicted in FIG. 10, the housing 1001 comprises a barrier wall 1009 configured to isolate the wire bonds 1007 from the flowing media. In some examples, the wire bonds 1007 may be coated in an encapsulant material.

As noted above, the flow sensing device 1000 comprises a PCBA 1003. In various examples, at least a surface of the example housing 1001 may be disposed/positioned adjacent a surface of the PCBA 1003. For example, as depicted in FIG. 10, one or more bottom surfaces of the housing 1001 of the flow sensing device 1000 are disposed adjacent a top surface of the PCBA 1003.

In various embodiments, at least a surface of the sensing element 1005 may be disposed adjacent a surface of the PCBA 1003. For example, as depicted, a bottom surface of the sensing element 1005 may be disposed adjacent (e.g., attached to) a top surface of the PCBA 1003. Additionally, in various examples, at least a portion of the sensing element 1005 may be disposed at least partially within the housing 1001 of the example flow sensing device 1000. In various examples, the PCBA 1003 may comprise one or more processing electronics and/or compensation circuitry (e.g., which may or may not include an ASIC). Such processing electronics may be electrically connected to terminals of the sensing element 1005, an ASIC (if present), and/or electrical terminals to process electrical signals from the example the sensing element 1005 and/or to transfer outputs from the example the sensing element 1005 to electronic components of one or more apparatuses used in conjunction with the flow sensing device 1000.

While the description above provides an example flow sensing device 1000, it is noted that the scope of the present disclosure is not limited to the description above. In some examples, an example flow sensing device 1000 may in accordance with the present disclosure may be in other forms. In some examples, an example flow sensing device 1000 may comprise one or more additional and/or alternative elements, and/or may be structured/positioned differently than that illustrated in FIG. 10.

Figure 11:
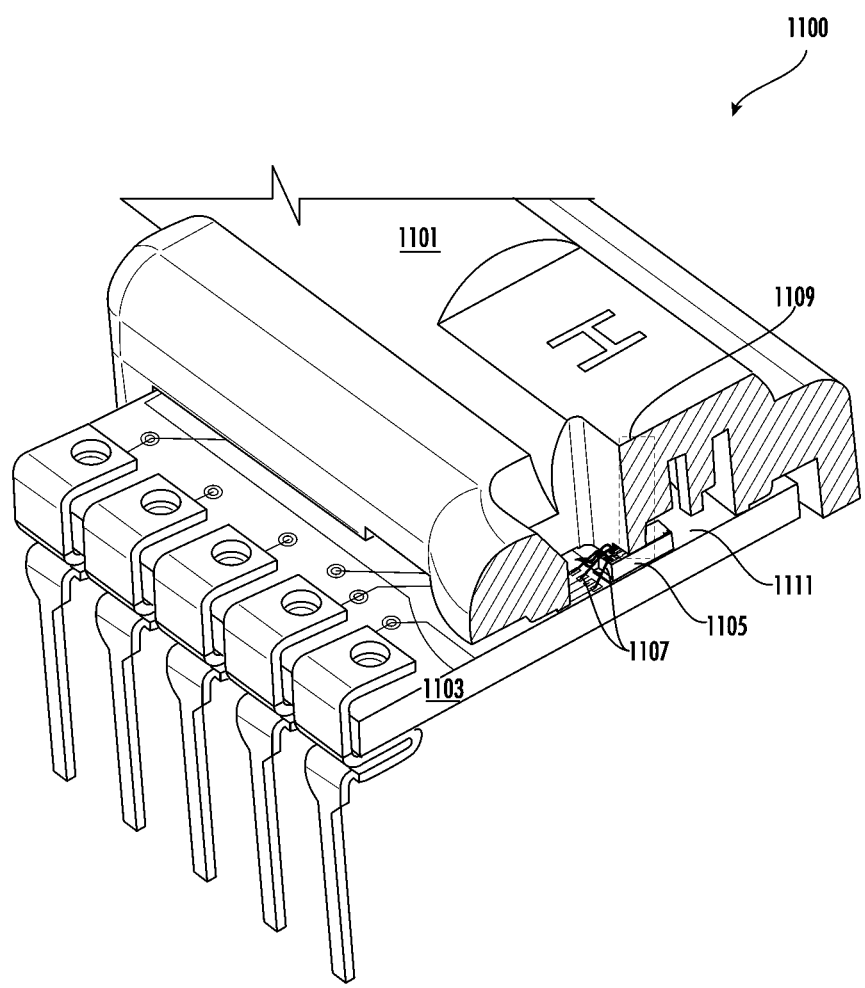
FIG. 11 illustrates a perspective view of an example flow sensing device, in accordance with examples of the present disclosure.

Referring now to FIG. 11, a schematic diagram depicting a perspective view of a portion of an example flow sensing device 1100 in accordance with various embodiments of the present disclosure is provided. The example flow sensing device 1100 may be similar to the flow sensing device 1100 described above in connection with FIG. 3. The example flow sensing device 1100 may be utilized to determine a high flow rate (e.g., a high flow rate between about 1 mL/hr and about 1000 mL/hr) associated with a flowing media. As depicted, the example flow sensing device 1100 comprises a housing 1101 defining an internal flow path/channel(s), a sensing element 1105 and a PCBA 1103.

As depicted in FIG. 11, the housing 1101 of the example flow sensing device 1100 may be or comprise a tubular shaped member defining an internal flow path/channel(s). In various embodiments, the example flow sensing device 1100 may be configured to convey a flowing media therethrough.

In various embodiments, the internal flow path/channel(s) of the flow sensing device 1100 may be or comprise a plurality of interconnected channels. In various examples, the internal flow path/channel(s) of the flow sensing device 1100 defines an angled geometry configured to direct the flowing media passing therethrough. For example, the plurality of interconnected channels may operate to laminarize the flow of a flowing media thereby improving a signal quality detected by the sensing element 1105 and eliminating extraneous noise. In various examples, at least one surface of the least one internal flow path/channel(s) may be disposed adjacent (e.g., near, close to, and/or the like) an example sensing element 1105 of the flow sensing device 1100.

As noted above, the flow sensing device 1100 comprises a sensing element 1105. The sensing element 1105 may be in electronic communication with the PCBA 1103. In various examples, the sensing element 1105 may be electrically connected to the PCBA 1103 using various techniques (e.g., wire bonds, bump bonds or the like) to electrically connect the sensing element 1105 to the PCBA 1103. As depicted in FIG. 11, the sensing element 1105 may be electrically connected to the PCBA 1103 via a plurality of wire bonds 1107. In some examples, the sensing element 1105 may be or comprise a microelectromechanical systems (MEMS) sensor. The example MEMS sensor may be suitable for a disposable component of an example flow sensing device 1100 as discussed herein. In various embodiments, the example MEMS sensor may be coated with an MEMS passivation material (e.g., silicon nitride). Accordingly, the passivation material may serve as the only barrier between the example MEMS sensor and a flowing media such that a signal quality detected by the example MEMS sensor is maximized.

In various embodiments, the flow sensing device 1100 may form part of and/or be connected to an external flow channel such that a flowing media can be conveyed therethrough. As depicted in FIG. 11, at least a surface of the housing 1101 (e.g., a surface of an internal flow path/channel(s)) may be at least partially disposed adjacent (e.g., near, close to, or the like) the sensing element 1105 of the flow sensing device 1100 such that at least a portion (e.g., sample) of the flowing media makes direct contact with the sensing element 1105. As depicted, the flowing media may be conveyed via an aperture 1111 disposed between a bottom surface of the housing 1101 and at least a portion of a top surface of the sensing element 1105. As further depicted, the aperture 1111 and at least one channel may comprise one or more fins. The example fins may operate to laminarize and direct a flow of a flowing medium within the at least one channel of the flow sensing device 1100 thereby producing a monotonic low noise, high-flow signal. In some examples, as depicted in FIG. 11, the housing 1101 comprises a barrier wall 1109 configured to isolate wire bonds 1107 of the sensing element from the flowing media. In some examples, the wire bonds 1107 may be coated in an encapsulate material.

As noted above, the flow sensing device 1100 comprises a PCBA 1103. In various examples, at least a surface of the example housing 1101 may be disposed/positioned adjacent a surface of the PCBA 1103. For example, as depicted in FIG. 11, one or more bottom surfaces of the housing 1101 of the flow sensing device 1100 are disposed adjacent a top surface of the PCBA 1103.

In various embodiments, at least a surface of the sensing element 1105 may be disposed adjacent a surface of the PCBA 1103. For example, as depicted, a bottom surface of the sensing element 1105 may be disposed adjacent (e.g., attached to) a top surface of the PCBA 1103. Additionally, in various examples, at least a portion of the sensing element 1105 may be disposed at least partially within the housing 1101 of the example flow sensing device 1100. In various examples, the PCBA 1103 may comprise one or more processing electronics and/or compensation circuitry (e.g., which may or may not include an ASIC). Such processing electronics may be electrically connected to terminals of the sensing element 1105, an ASIC (if present), and/or electrical terminals to process electrical signals from the example the sensing element 1105 and/or to transfer outputs from the example the sensing element 1105 to electronic components of one or more apparatuses used in conjunction with the flow sensing device 1100.

While the description above provides an example flow sensing device 1100, it is noted that the scope of the present disclosure is not limited to the description above. In some examples, an example flow sensing device 1100 may in accordance with the present disclosure may be in other forms. In some examples, an example flow sensing device 1100 may comprise one or more additional and/or alternative elements, and/or may be structured/positioned differently than that illustrated in FIG. 11.

Figure 12:
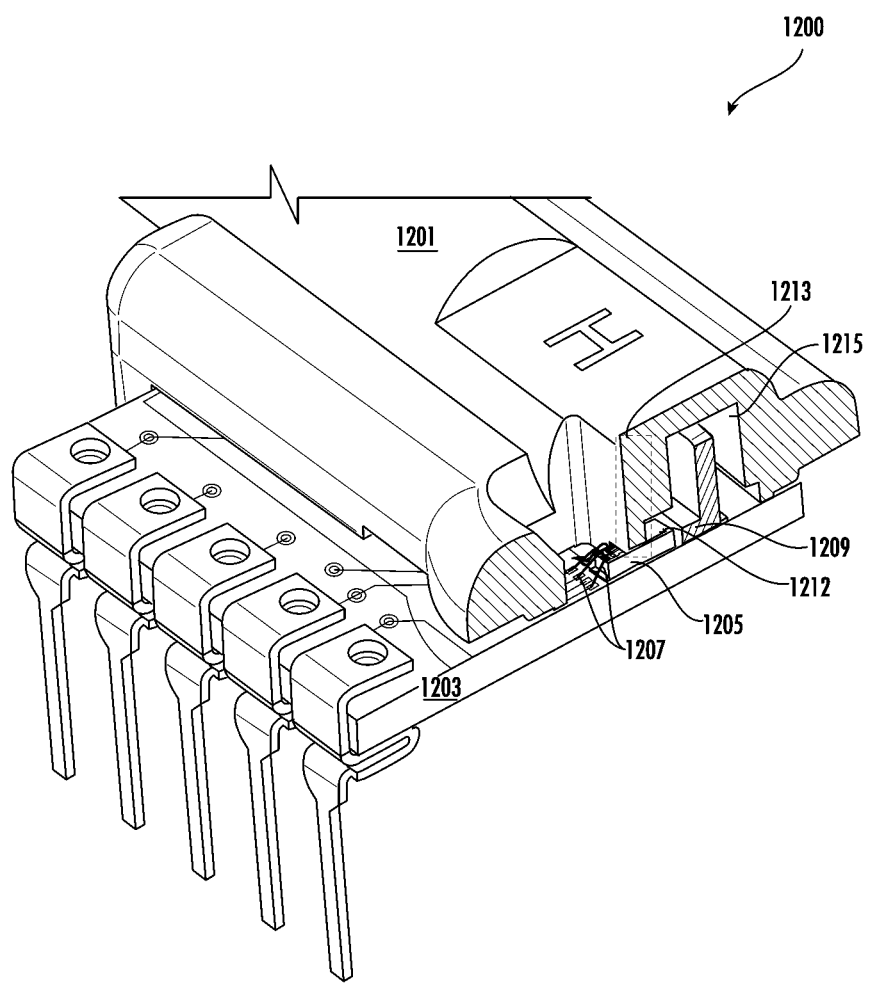
FIG. 12 illustrates a perspective view of an example flow sensing device, in accordance with examples of the present disclosure.

Referring now to FIG. 12, a schematic diagram depicting a perspective view of a portion of an example flow sensing device 1200 in accordance with various embodiments of the present disclosure is provided. The example flow sensing device 1200 may be similar to the flow sensing device 500 described above in connection with FIG. 5. The example flow sensing device 1200 may be utilized to determine a high flow rate (e.g., a high flow rate between about 1 mL/hr and about 1000 mL/hr) associated with a flowing media. As depicted, the example flow sensing device 1200 comprises a housing 1201 defining an internal flow path 1215 comprising one ore more channel(s), a PCBA 1203, a sensing element 1205 and a shielding element 1209.

As depicted in FIG. 12, the housing 1201 of the example flow sensing device 1200 may be or comprise a tubular shaped member defining the internal flow path 1215/channel(s). In various embodiments, the example flow sensing device 1200 may be configured to convey a flowing media therethrough.

In various embodiments, the internal flow path 1215 of the flow sensing device 1200 may be or comprise a plurality of interconnected channels. In various examples, at least a portion of the internal flow path 1215 of the flow sensing device 1200 may define an angled geometry configured to direct the flowing media passing therethrough. For example, the plurality of interconnected channels may operate to laminarize the flow of a flowing media thereby improving a signal quality detected by the sensing element 1205 and eliminating extraneous noise. In various examples, at least one surface of the internal flow path 1215 may be disposed adjacent (e.g., near, close to, and/or the like) the example sensing element 1205 of the flow sensing device 1200 such that at least a portion of a flowing media makes direct contact with the sensing element 1205 as it traverses the internal flow path 1215.

As noted above, the flow sensing device 1200 comprises a shielding element 1209. The shielding element 1209 may define at least a portion of the internal flow path 1215 of the flow sensing device 1200. For example, as depicted, the shielding element 1209 may be a distinct element defining at least one channel within the housing 1201 of the flow sensing device 1200. As depicted, the shielding element 1209 may comprise a fin defining a first proximate aperture adjacent the sensing element 1205 and a second distal aperture removed from the sensing element 1205. The example shielding element 1209/fin may operate to laminarize and direct a flow of a flowing medium within the at least one channel of the flow sensing device 1200 thereby producing a monotonic low noise, high-flow signal. In some examples, as depicted in FIG. 12, the housing 1201 comprises a barrier wall 1213 configured to isolate wire bonds 1207 of the sensing element from the flowing media. In some examples, the wire bonds 1207 may be coated in an encapsulate material. In various embodiments, the shielding element 1209 may operate to regulate (e.g., limit, channel, direct, laminarize, and/or the like) an amount and/or flow of a flowing media making direct contact with the sensing element 1205. Additionally, in some examples, one or more surfaces of the example an internal flow path 1215 of the housing 1201 and/or shielding element 1209 may be utilized to shield at least a portion or surface of the sensing element 1205. In various examples, as depicted, the shielding element 1209 may be disposed adjacent (e.g., near, close to and/or the like) the sensing element 1205 in order to provide a shield around the sensing element 1205, thereby improving part-to-part performance of the flow sensing device 1200.

As noted above, the flow sensing device 1200 comprises a sensing element 1205. The sensing element 1205 may be in electronic communication with the PCBA 1203. In various examples, the sensing element 1205 may be electrically connected to the PCBA 1203 using various techniques (e.g., wire bonds, bump bonds or the like) to electrically connect the sensing element 1205 to the PCBA 1203. As depicted in FIG. 12, the sensing element 1205 may be electrically connected to the PCBA 1203 via a plurality of wire bonds 1207. In some examples, the sensing element 1205 may be or comprise a microelectromechanical systems (MEMS) sensor. The example MEMS sensor may be suitable for a disposable flow sensing device 1200 as discussed elsewhere herein. In various embodiments, the example MEMS sensor may be coated with an MEMS passivation material (e.g., silicon nitride). Accordingly, the passivation material may serve as the only barrier between the example MEMS sensor and a flowing media such that a signal quality detected by the example MEMS sensor is maximized.

In various embodiments, the flow sensing device 1200 may form part of and/or be connected to an external flow channel such that a flowing media can be conveyed therethrough. As depicted in FIG. 12, at least a surface of the housing 1201 (e.g., a surface of an internal flow path/channel(s)) may be at least partially disposed adjacent (e.g., near, close to, or the like) the sensing element 1205 of the flow sensing device 1200 such that at least a portion (e.g., sample) of the flowing media makes direct contact with the sensing element 1205.

As noted above, the flow sensing device 1200 comprises a PCBA 1203. In various examples, at least a surface of the example housing 1201 may be disposed/positioned adjacent a surface of the PCBA 1203. For example, as depicted in FIG. 12, one or more bottom surfaces of the housing 1201 of the flow sensing device 1200 are disposed adjacent a top surface of the PCBA 1203.

In various embodiments, at least a surface of the sensing element 1205 may be disposed adjacent a surface of the PCBA 1203. For example, as depicted, a bottom surface of the sensing element 1205 may be disposed adjacent (e.g., attached to) a top surface of the PCBA 1203. Additionally, in various examples, at least a portion of the sensing element 1205 may be disposed at least partially within the housing 1201 of the example flow sensing device 1200. In various examples, the PCBA 1203 may comprise one or more processing electronics and/or compensation circuitry (e.g., which may or may not include an ASIC). Such processing electronics may be electrically connected to terminals of the sensing element 1205, an ASIC (if present), and/or electrical terminals to process electrical signals from the example the sensing element 1205 and/or to transfer outputs from the example the sensing element 1205 to electronic components of one or more apparatuses used in conjunction with the flow sensing device 1200.

While the description above provides an example flow sensing device 1200, it is noted that the scope of the present disclosure is not limited to the description above. In some examples, an example flow sensing device 1200 may in accordance with the present disclosure may be in other forms. In some examples, an example flow sensing device 1200 may comprise one or more additional and/or alternative elements, and/or may be structured/positioned differently than that illustrated in FIG. 12.

Figure 13:
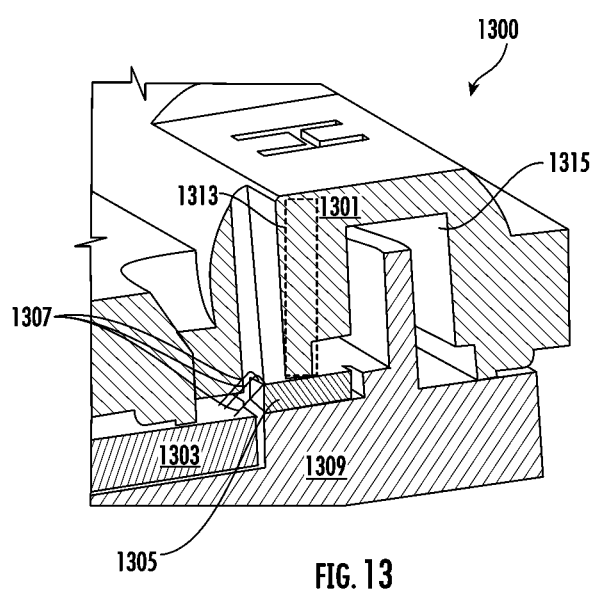
FIG. 13 illustrates a perspective view of an example flow sensing device, in accordance with examples of the present disclosure.

Referring now to FIG. 13, a schematic diagram depicting a perspective view of a portion of an example flow sensing device 1300 in accordance with various embodiments of the present disclosure is provided. The example flow sensing device 1300 may be similar to the flow sensing device 500 described above in connection with FIG. 5. The example flow sensing device 1300 may be utilized to determine a high flow rate (e.g., a high flow rate between about 1 mL/hr and about 1000 mL/hr) associated with a flowing media. As depicted, the example flow sensing device 1300 comprises a housing 1301 defining an internal flow path 1315 comprising one or more channels, a PCBA 1303, a sensing element 1305 and a shielding element 1309.

As depicted in FIG. 13, the housing 1301 of the example flow sensing device 1300 may be or comprise a tubular shaped member defining an internal flow path 1315). In various embodiments, the example flow sensing device 1300 may be configured to convey a flowing media therethrough.

In various embodiments, the internal flow path 1315 of the flow sensing device 1300 may be or comprise a plurality of interconnected channels. In various examples, the internal flow path 1315 of the flow sensing device 1300 defines an angled geometry configured to direct the flowing media passing therethrough. For example, the plurality of interconnected channels may operate to laminarize the flow of a flowing media thereby improving a signal quality detected by the sensing element 1305 and eliminating extraneous noise. In various examples, at least one surface of the least one internal flow path/channel(s) may be disposed adjacent (e.g., near, close to, and/or the like) the example sensing element 1305 of the flow sensing device 1300 such that at least a portion of a flowing media makes direct contact with the sensing element 1305 as it traverses the internal flow path 1315.

As noted above, the flow sensing device 1300 comprises a shielding element 1309. The shielding element 1309 and the housing 1301 may define two separate elements or portions of the flow sensing device 1300. In some examples, as depicted, the shielding element 1309 may be a distinct element defining at least a first portion of the internal flow path 1315/channel(s) within the housing 1301 of the flow sensing device 1300. Additionally, the shielding element 1309 may define at least a second portion of the internal flow path 1315/channel(s) of the flow sensing device 1300. As depicted, the shielding element 1309 may comprise a fin defining a proximate aperture adjacent the sensing element 1305 and a distal aperture removed from the sensing element 1305. The example fin may operate to laminarize and direct a flow of a flowing medium within the at least one channel of the flow sensing device 1300 thereby producing a monotonic low noise, high-flow signal.

In some examples, as depicted in FIG. 13, the housing 1301 comprises a barrier wall 1313 configured to isolate wire bonds 1307 of the sensing element from the flowing media. In some examples, the wire bonds 1307 may be coated in an encapsulate material. In various embodiments, the shielding element 1309 may be configured to regulate (e.g., limit, channel, direct, laminarize, and/or the like) an amount and/or flow of a flowing media making direct contact with the sensing element 1305. Additionally, in some examples, one or more surfaces of the example an internal flow path 1315/channel(s) of the housing 1301 and/or shielding element 1309 may be utilized to shield at least a portion and/or surface of the sensing element 1305. In various examples, the shielding element 1309 may be disposed adjacent (e.g., near, close to and/or the like) the sensing element 1305 in order to provide a shield around at least a portion of the sensing element 1305, thereby improving part-to-part performance of the flow sensing device 1300. As depicted, a bottom surface of the sensing element 1305 may be disposed adjacent a surface of the shielding element 1309. Additionally, as depicted, a top surface of the sensing element 1305 may be disposed adjacent a bottom surface of the housing 1301. Additionally, as depicted, at least a portion or surface of the shielding element 1309 may be in contact with the PCBA 1303. In some examples, the shielding element 1309 may comprise a molded-in leadframe. In various examples, the shielding element 1309 and/or housing 1301 may be or comprise plastic materials, biocompatible materials and/or the like.

As noted above, the flow sensing device 1300 comprises a sensing element 1305. The sensing element 1305 may be in electronic communication with the PCBA 1303. In various examples, the sensing element 1305 may be electrically connected to the PCBA 1303 using various techniques (e.g., wire bonds, bump bonds or the like) to electrically connect the sensing element 1305 to the PCBA 1303. As depicted in FIG. 13, the sensing element 1305 may be electrically connected to the PCBA 1303 via a plurality of wire bonds 1307. In some examples, the sensing element 1305 may be or comprise a microelectromechanical systems (MEMS) sensor. The example MEMS sensor may be suitable for a modular flow sensing device 1300 as discussed elsewhere herein. In various embodiments, the example MEMS sensor may be coated with an MEMS passivation material (e.g., silicon nitride). Accordingly, the passivation material may serve as the only barrier between the example MEMS sensor and a flowing media such that a signal quality detected by the example MEMS sensor is maximized.

In various embodiments, the flow sensing device 1300 may form part of and/or be connected to an external flow channel such that a flowing media can be conveyed therethrough. As depicted in FIG. 13, at least a surface of the housing 1301 (e.g., a surface of an internal flow path 1315/channel(s)) may be at least partially disposed adjacent (e.g., near, close to, or the like) the sensing element 1305 of the flow sensing device 1300 such that at least a portion (e.g., sample) of the flowing media makes direct contact with the sensing element 1305.

As noted above, the flow sensing device 1300 comprises a PCBA 1303. In various examples, at least a surface of the example housing 1301 may be disposed/positioned adjacent a surface of the PCBA 1303. For example, as depicted in FIG. 13, one or more bottom surfaces of the housing 1301 of the flow sensing device 1300 are disposed adjacent a top surface of the PCBA 1303.

In various embodiments, at least a surface of the sensing element 1305 may be disposed adjacent a surface of the PCBA 1303. For example, as depicted, a bottom surface of the sensing element 1305 may be disposed adjacent (e.g., attached to) a top surface of the PCBA 1303. Additionally, in various examples, at least a portion of the sensing element 1305 may be disposed at least partially within the housing 1301 of the example flow sensing device 1300. In various examples, the PCBA 1303 may comprise one or more processing electronics and/or compensation circuitry (e.g., which may or may not include an ASIC). Such processing electronics may be electrically connected to terminals of the sensing element 1305, an ASIC (if present), and/or electrical terminals to process electrical signals from the example the sensing element 1305 and/or to transfer outputs from the example the sensing element 1305 to electronic components of one or more apparatuses used in conjunction with the flow sensing device 1300.

While the description above provides an example flow sensing device 1300, it is noted that the scope of the present disclosure is not limited to the description above. In some examples, an example flow sensing device 1300 may in accordance with the present disclosure may be in other forms. In some examples, an example flow sensing device 1300 may comprise one or more additional and/or alternative elements, and/or may be structured/positioned differently than that illustrated in FIG. 13.

Figure 14:
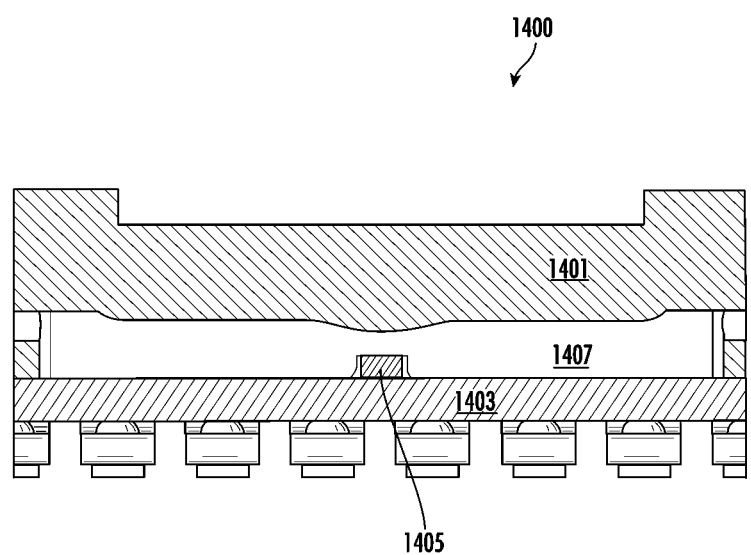
FIG. 14 illustrates a cross-sectional view of an example flow sensing device, in accordance with examples of the present disclosure.

Referring now to FIG. 14, a schematic diagram depicting a side cross-sectional view of a portion of an example flow sensing device 1400 in accordance with various embodiments of the present disclosure is provided. The example flow sensing device 1400 may be similar to the flow sensing device 100 described above in connection with FIG. 1. As depicted, the example flow sensing device 1400 comprises a housing 1401 defining an internal flow path/channel(s), a PCBA 1403 and a sensing element 1405.

As depicted in FIG. 14, the housing 1401 of the example flow sensing device 1400 may be or comprise a tubular shaped member defining an internal flow path/channel(s) 1407. In various embodiments, the example flow sensing device 1400 may be configured to convey a flowing media therethrough.

In various embodiments, the internal flow path/channel(s) of the flow sensing device 1400 may be or comprise a plurality of interconnected channels. As depicted, the internal flow path/channel(s) 1407 of the flow sensing device 1400 may define an angled geometry (i.e., non-planar geometry) configured to direct the flowing media passing therethrough. For example, the plurality of interconnected channels may operate to laminarize the flow of a flowing media thereby improving a signal quality detected by the sensing element 1405 and eliminating extraneous noise. In various examples, at least one surface of the least one internal flow path/channel(s) may be disposed adjacent (e.g., near, close to, and/or the like) the example sensing element 1405 of the flow sensing device 1400. As depicted, the sensing element 1405 may be at least partially disposed within the internal flow path/channel(s) 1407 such that at least a surface of the sensing element 1405 forms a portion of the internal flow path/channel(s).

As noted above, the flow sensing device 1400 comprises a sensing element 1405. The sensing element 1405 may be in electronic communication with the PCBA 1403. In various examples, the sensing element 1405 may be electrically connected to the PCBA 1403 using various techniques (e.g., wire bonds, bump bonds or the like) to electrically connect the sensing element 1405 to the PCBA 1403. In some examples, the sensing element 1405 may be or comprise a MEMS sensor. The example MEMS sensor may be suitable for a modular (e.g., disposable) flow sensing device 1400, as discussed elsewhere herein.

In various embodiments, the flow sensing device 1400 may form part of and/or be connected to an external flow channel such that a flowing media can be conveyed therethrough. As depicted in FIG. 14, at least a surface of the housing 1401 (e.g., a surface of an internal flow path/channel(s)) may be at least partially disposed adjacent (e.g., near, close to, or the like) the sensing element 1405 of the flow sensing device 1400 such that at least a portion (e.g., sample) of the flowing media makes direct contact with the sensing element 1405.

As noted above, the flow sensing device 1400 comprises a PCBA 1403. In various examples, at least a surface of the example housing 1401 may be disposed/positioned adjacent a surface of the PCBA 1403. For example, as depicted in FIG. 14, at least one bottom surface of the housing 1401 of the flow sensing device 1400 is disposed adjacent a top surface of the PCBA 1403.

In various embodiments, at least a surface of the sensing element 1405 may be disposed adjacent a surface of the PCBA 1403. For example, as depicted, a bottom surface of the sensing element 1405 may be disposed adjacent (e.g., attached to) a top surface of the PCBA 1403. Additionally, in various examples, at least a portion of the sensing element 1405 may be disposed at least partially within the housing 1401 of the example flow sensing device 1400. In various examples, the PCBA 1403 may comprise one or more processing electronics and/or compensation circuitry (e.g., which may or may not include an ASIC). Such processing electronics may be electrically connected to terminals of the sensing element 1405, an ASIC (if present), and/or electrical terminals to process electrical signals from the example the sensing element 1405 and/or to transfer outputs from the example the sensing element 1405 to electronic components of one or more apparatuses used in conjunction with the flow sensing device 1400.

While the description above provides an example flow sensing device 1400, it is noted that the scope of the present disclosure is not limited to the description above. In some examples, an example flow sensing device 1400 may in accordance with the present disclosure may be in other forms. In some examples, an example flow sensing device 1400 may comprise one or more additional and/or alternative elements, and/or may be structured/positioned differently than that illustrated in FIG. 14.

In many settings requiring extreme cleanliness (e.g., clinical applications), a flow sensing device (e.g., a flow sensing device comprising a sterile transducer element) may be exposed to unsanitary environmental conditions in the course of use. As a result, the example flow sensing device may require cleaning. In various embodiments, flow sensing devices may include adhesives and other materials that are sensitive to high heat, humidity and/or cleaning agents which may damage the flow sensing devices and/or sensing elements (e.g., a transducer element such as a micro-electro-mechanical systems (MEMS)-based transducer). Accordingly, in some examples, known cleaning techniques may expose such flow sensing devices to harsh environmental conditions (e.g., electronic beam (e-beam) irradiation, high heat and/or high humidity, harsh chemicals, and/or the like) that may result in damage to the example flow sensing device.

In some examples, an example sensing element of a flow sensing device may be intimately connected to compensation circuitry either directly, through a substrate or package wiring. An example sensing element (e.g., MEMS-based transducers including fluid flow transducers, pressure and/or humidity transducers) may be characterized by unique sensing characteristics and output signals in response to a physical parameter and/or media being measured. Due to the characteristics of the example sensing element and the input stage of the interface electronics of compensation circuitry, such sensing elements and compensation systems are typically calibrated together while controlling the physical parameters being compensated. In some cases, a flow sensing device including compensation circuitry may be damaged by cleaning conditions, described above, resulting in disposal of the entire flow sensing device along with the compensation circuitry which may be expensive and onerous to calibrate.

In various embodiments of the present disclosure, a modular flow sensing device comprising a sensing element separated from other circuitry (e.g., compensation circuitry) may be provided. In some embodiments, the sensing element (e.g., transducer element) and the other circuitry (e.g., compensation circuitry) may be separated within a package such that at least a portion of the sensing element may be exposed to a media (e.g., flowing media). An example modular flow sensing device may comprise one or more removeable and/or disposable components/modules. In various examples, the disposable component may be mated with other processing circuitry such that an accurate output signal can be generated. In various embodiments, a disposable component and a non-disposable component may each comprise processing circuitry and memory so as to generate required operational information/data (e.g., coefficients) when mated providing a highly accurate device and system capable of communicating with external apparatuses (e.g., pumps, equipment and/or the like).

Figure 15:
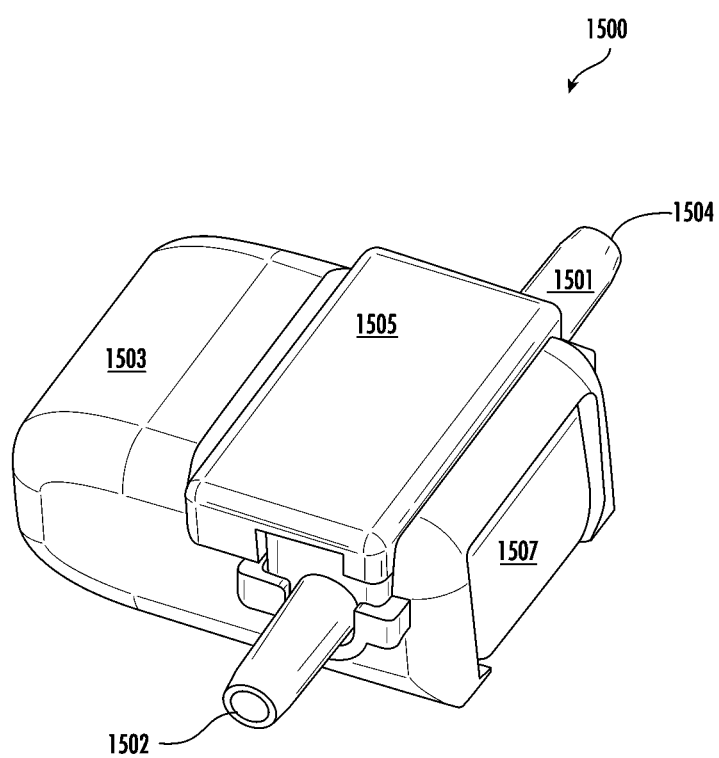
FIG. 15 illustrates a perspective view of an example flow sensing assembly, in accordance with examples of the present disclosure.

Referring now to FIG. 15, a schematic diagram depicting an example flow sensing assembly 1500 in accordance with various embodiments of the present disclosure is provided. In particular, the flow sensing assembly 1500 defines a housing comprising a first component (e.g., a disposable component) 1505, a flow sensing device 1501, a second component (e.g., a non-disposable component) 1503 and a securing element 1507. In some examples, dimensions of the flow sensing assembly 1500 may be approximately 1.5 inches×1.5 inches×0.5 inches.

As depicted, the first component (e.g., the disposable component) 1505 comprises a flow sensing device 1501. The flow sensing device 1501 may be similar to the flow sensing device 100 described above in relation to FIG. 1 and/or other flow sensing devices described herein. The flow sensing device 1501 may be or comprise a tubular shaped member configured to convey a flowing media from an inlet 1502 of the flow sensing device 1501 to an outlet 1504 of the flow sensing device 1501. In various embodiments, the flow sensing device 1501 may form part of and/or be connected to an external flow channel (e.g., via a first tube connected to the inlet 1502 and a second tube connected to the outlet 1504) such that a flowing media can be conveyed therethrough.

As noted above, the example flow sensing assembly 1500 comprises a second component (e.g., a non-disposable component) 1503. In some embodiments, as depicted, the second component (e.g., the non-disposable component) 1503 comprises a flow sensing device 1501. In other examples, the second component (e.g., the non-disposable component) 1503 and the flow sensing device 1501 may be distinct components. In various examples, the second component (e.g., the non-disposable component) 1503 and the flow sensing device 1501 may be removably attached to one another.

In various embodiments, the second component (e.g., the non-disposable component) 1503 comprises processing circuitry, one or more processing electronics, and/or compensation circuitry (e.g., which may or may not include an ASIC, such as a mixed-signal ASIC or analog ASIC). Additionally, the second component (e.g., the non-disposable component) 1503 may be or comprise one or more memories (e.g., Ferroelectric Random Access Memory (FRAM)), an analog front-end controller (AFEC), an analog-to-digital converter (ADC), heating control circuitry, and/or the like. In various embodiments, the second component (e.g., the non-disposable component) 1503 may be electrically connected to the first component (e.g., the disposable component) 1505 to process electrical signals received from the first component (e.g., the disposable component) 1505 and/or to transfer outputs from the first component (e.g., the disposable component) 1505 into a particular output format. For example, circuitry of the second component (e.g., the non-disposable component) 1503 may be configured to format the output signal provided by the example first/disposable component 1505 into a ratiometric output format, a current format, a digital output format and/or any other suitable format. In some cases, the circuitry of the second component (e.g., the non-disposable component) 1503 may be configured to provide an output to one or more electrical terminals facilitating electrical connections with electronic components of one or more apparatuses used in conjunction with the flow sensing assembly 1500. For example, the second component (e.g., the non-disposable component) 1503 may be in wired or wireless communication (e.g., Bluetooth) with an infusion pump. By way of example, when the first component (e.g., the disposable component) 1505 is electrically connected to the second component (e.g., the non-disposable component) 1503, the one or more memories of the second component (e.g., the non-disposable component) 1503 may be used by the second component (e.g., the non-disposable component) to generate necessary coefficients for compensation required by the first component (e.g., the disposable component) 1503. In one example, an electrical response to flowing media and temperature may be used to compensate for the temperature dependence of the first component (e.g., the disposable component) 1505 (e.g., a sensing element of the first component (e.g., a disposable component)). In some examples, as discussed herein, an example flow sensing assembly 1500 may comprise a heating element. In such examples, the second component (e.g., the non-disposable component) 1503 may comprise heating control circuitry/elements.

As noted above, the example flow sensing assembly 1500 comprises a first component (e.g., a disposable component) 1505. In some embodiments, as depicted, the first component (e.g., the disposable component) 1505 may be removably connected to the second component (e.g., the non-disposable component) 1503/flow sensing device 1501 via a securing element 1507. As depicted in FIG. 15, the flow sensing assembly 1500 comprises a securing element 1507 disposed on a surface of the flow sensing assembly 1500 for actuating release of the first component (e.g., the disposable component) 1505 from the second component (e.g., the non-disposable component) 1503. The securing element 1507 may be or comprise a retaining clip, spring-based mechanism, and/or any other suitable mechanism for removably securing/attaching the first component (e.g., the disposable component) 1505 to the second component (e.g., the non-disposable component) 1503. In some examples, as depicted, the securing element 1507 comprises a push button for actuating release of the first component (e.g., the disposable component) 1505 from the second component (e.g., the non-disposable component) 1503.

In various embodiments, the first component (e.g., the disposable component) 1505 may comprise a sensing element. The example sensing element may be similar to the sensing element 205 described above in connection with FIG. 2. The example sensing element may be or comprise a MEMS sensor. The example sensing element may be at least partially disposed within a flow path of the example flow sensing device 1501. The example sensing element may comprise one or more circuitries, including, but not limited to, temperature sensing circuitry, communication circuitry (for example, near field communication (NFC) circuitry), and/or power control circuitry, and/or the like. The example first/disposable component 1505 may be in electronic communication with the second component (e.g., the non-disposable component) 1503.

While the description above provides an example flow sensing assembly 1500, it is noted that the scope of the present disclosure is not limited to the description above. In some examples, an example flow sensing assembly 1500 may in accordance with the present disclosure may be in other forms. In some examples, an example flow sensing assembly 1500 may comprise one or more additional and/or alternative elements, and/or may be structured/positioned differently than that illustrated in FIG. 15.

Figure 16:
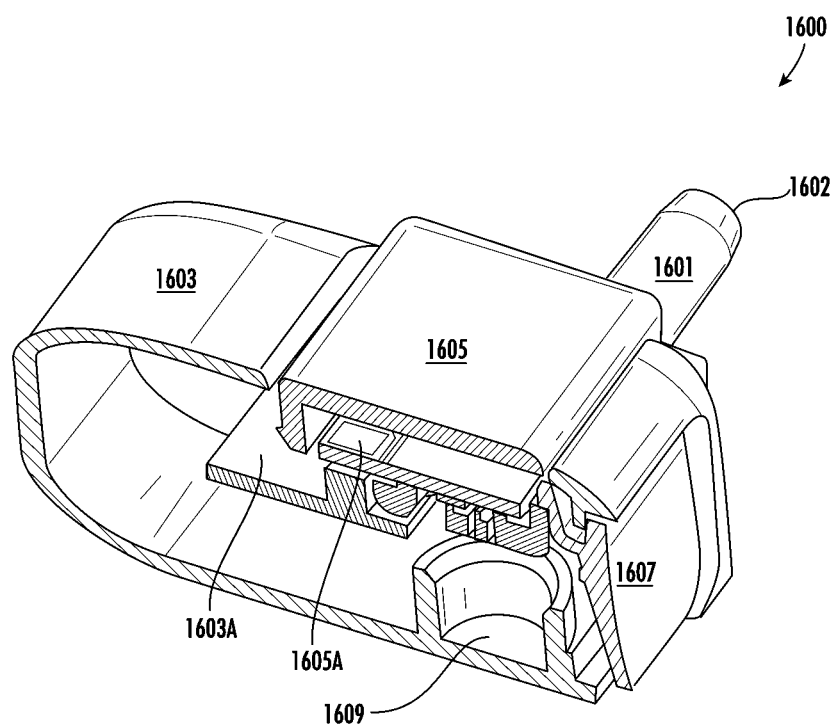
FIG. 16 illustrates a perspective cross-sectional view of an example flow sensing device, in accordance with examples of the present disclosure.

Referring now to FIG. 16, a schematic diagram depicting a perspective cross-sectional view of an example flow sensing assembly 1600 in accordance with various embodiments of the present disclosure is provided. The flow sensing assembly 1600 may be similar to the flow sensing assembly 1500 described above in connection with FIG. 15. As depicted in FIG. 16, the flow sensing assembly 1600 defines a housing comprising a first component (e.g., a disposable component) 1605, a flow sensing device 1601, a second component (e.g., a non-disposable component) 1603 and a securing element 1607.

As depicted, the first component (e.g., the disposable component) 1605 comprises the flow sensing device 1601. The flow sensing device 1601 may be or comprise a tubular shaped member configured to convey a flowing media from an inlet 1602 of the flow sensing device 1601 to an outlet of the flow sensing device 1601. In various embodiments, the flow sensing device 1601 may form part of and/or be connected to an external flow channel (e.g., via a first tube connected to the inlet 1602 and a second tube connected to the outlet 1604) such that a flowing media can be conveyed therethrough.

As noted above, the example flow sensing assembly 1600 comprises a second component (e.g., a non-disposable component) 1603. In some embodiments, as depicted, the second component (e.g., the non-disposable component) 1603 and the flow sensing device 1601 may define a unitary body. In other examples, the second component (e.g., the non-disposable component) 1603 and the flow sensing device 1601 may be distinct components. For example, the second component (e.g., the non-disposable component) 1603 and the flow sensing device 1601 may be removably attached to one another.

As depicted, at least a surface of the first component (e.g., the disposable component) 1605 defines a portion of a top surface of the flow sensing assembly 1600 housing. As depicted, the second component (e.g., the non-disposable component) 1603 comprises a PCBA 1603A. Similarly, the first component (e.g., the disposable component) 1605 comprises a PCBA 1605A. As depicted, a bottom surface of the PCBA 1603A is disposed adjacent a top surface of the PCBA 1603A.

In various embodiments, the second component (e.g., the non-disposable component) 1603 (e.g., PCBA 1603A) comprises processing circuitry, one or more processing electronics, and/or compensation circuitry (e.g., which may or may not include an ASIC, such as a mixed-signal ASIC or analog ASIC). Additionally, the second component (e.g., the non-disposable component) 1603 may be or comprise one or more memories (e.g., Ferroelectric Random Access Memory (FRAM)), an analog front-end controller (AFEC), an analog-to-digital converter (ADC), heating control circuitry, and/or the like. In various embodiments, the second component (e.g., the non-disposable component) 1603 (e.g., PCBA 1603A) may be electrically connected to the first component (e.g., the disposable component) 1605 (e.g., PCBA 1605A) to process electrical signals received from the first component (e.g., the disposable component) 1605 and/or to transfer outputs from the first component (e.g., the disposable component) 1605 into a particular output format. For example, circuitry of the second component (e.g., the non-disposable component) 1603 may be configured to format the output signal provided by the example first component 1605 into a ratio-metric output format, a current format, a digital output format and/or any other suitable format. In some cases, the circuitry of the second component (e.g., the non-disposable component) 1603 may be configured to provide an output to one or more electrical terminals facilitating electrical connections with electronic components of one or more apparatuses used in conjunction with the flow sensing assembly 1600. For example, the second component (e.g., the non-disposable component) 1603 may be in wired or wireless communication (e.g., Bluetooth) with an infusion pump. By way of example, when the first component (e.g., the disposable component) 1605 is electrically connected to the second component (e.g., the non-disposable component) 1603, the one or more memories of the second component (e.g., the non-disposable component) 1603 may be used by the second component (e.g., the non-disposable component) to generate necessary coefficients for compensation required by the first component (e.g., the disposable component) 1605. In one example, an electrical response to flowing media and temperature may be used to compensate for the temperature dependence of the first component (e.g., the disposable component) 1605 (e.g., a sensing element of the first component (e.g., a disposable component)). In some examples, as discussed herein, an example flow sensing assembly 1600 may comprise a heating element. In such examples, the second component (e.g., the non-disposable component) 1603 may comprise heating control circuitry/elements.

As noted above, the example flow sensing assembly 1600 comprises a first component (e.g., a disposable component) 1605. In some embodiments, as depicted, the first component (e.g., the disposable component) 1605 may be removably connected to the second component (e.g., the non-disposable component) 1603 via a securing element 1607. As depicted in FIG. 16, the flow sensing assembly 1600 comprises a securing element 1607 disposed on a surface of the flow sensing assembly 1600 for actuating release of the first component (e.g., the disposable component) 1605 from the second component (e.g., the non-disposable component) 1603. The securing element 1607 may be or comprise a retaining clip, spring-based mechanism, and/or any other suitable mechanism for removably securing/attaching the first component (e.g., the disposable component) 1605 to the second component (e.g., the non-disposable component) 1603. In some examples, as depicted, the securing element 1607 comprises a push button for actuating release of the first component (e.g., the disposable component) 1605 from the second component (e.g., the non-disposable component) 1603.

In various embodiments, the first component (e.g., the disposable component) 1605 may comprise a sensing element. The example sensing element may be similar to the sensing element 205 described above in connection with FIG. 2. The example sensing element may be or comprise a MEMS sensor. The example sensing element may be at least partially disposed within a flow path of the example flow sensing device 1601. The example sensing element may comprise one or more circuitries, including, but not limited to, temperature sensing circuitry, communication circuitry (for example, near field communication (NFC) circuitry), and/or power control circuitry, and/or the like. The example first/disposable component 1605 may be in electronic communication with the second component (e.g., the non-disposable component) 1603.

While the description above provides an example flow sensing assembly 1600, it is noted that the scope of the present disclosure is not limited to the description above. In some examples, an example flow sensing assembly 1600 may in accordance with the present disclosure may be in other forms. In some examples, an example flow sensing assembly 1600 may comprise one or more additional and/or alternative elements, and/or may be structured/positioned differently than that illustrated in FIG. 16.

Figure 17:
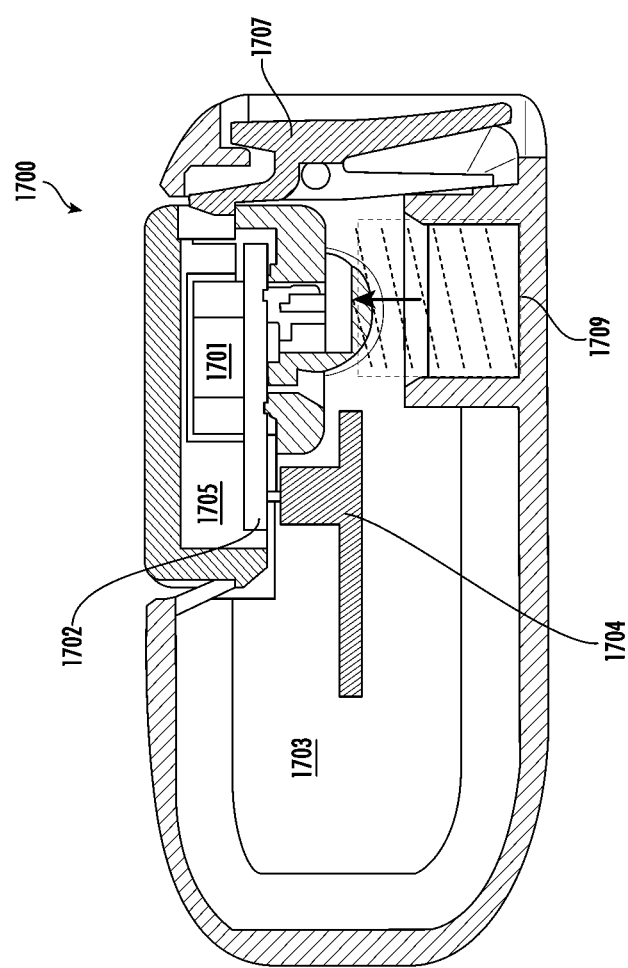
FIG. 17 illustrates a cross-sectional view of an example flow sensing device assembly, in accordance with examples of the present disclosure.

Referring now to FIG. 17, a schematic diagram depicting a side cross-sectional view of an example flow sensing assembly 1700 in accordance with various embodiments of the present disclosure is provided. The flow sensing assembly 1700 may be similar/identical to the flow sensing assembly 1600 described above in connection with FIG. 16. As depicted in FIG. 17, the flow sensing assembly 1700 defines a housing comprising a first component (e.g., a disposable component) 1705 comprising a flow sensing device 1701, a second component (e.g., a non-disposable component) 1703 and a securing element 1707.

As depicted, the first component (e.g., the disposable component) 1705 comprises the flow sensing device 1701. The flow sensing device 1701 may be or comprise a tubular shaped member configured to convey a flowing media from an inlet 1702 of the flow sensing device 1701 to an outlet 1704 of the flow sensing device 1701. In various embodiments, the flow sensing device 1701 may form part of and/or be connected to an external flow channel (e.g., via a first tube connected to the inlet 1702 and a second tube connected to the outlet 1704) such that a flowing media can be conveyed therethrough.

As noted above, the example flow sensing assembly 1700 comprises a second component (e.g., a non-disposable component) 1703. In some embodiments, as depicted, the second component (e.g., the non-disposable component) 1703 and the flow sensing device 1701 may define a unitary body. In other examples, the second component (e.g., the non-disposable component) 1703 and the flow sensing device 1701 may be distinct components. For example, the second component (e.g., the non-disposable component) 1703 and the flow sensing device 1701 may be removably attached to one another.

As depicted, at least a surface of the first component (e.g., the disposable component) 1705 defines a portion of a top surface of the flow sensing assembly 1700 housing. As depicted, the second component (e.g., the non-disposable component) 1703 comprises a PCBA 1703A. Similarly, the first component (e.g., the disposable component) 1705 comprises a PCBA 1705A. As depicted, a bottom surface of the PCBA 1703A is disposed adjacent a top surface of the PCBA 1703A.

In various embodiments, the second component (e.g., the non-disposable component) 1703 (e.g., PCBA 1703A) comprises processing circuitry, one or more processing electronics, and/or compensation circuitry (e.g., which may or may not include an ASIC, such as a mixed-signal ASIC or analog ASIC). Additionally, the second component (e.g., the non-disposable component) 1703 may be or comprise one or more memories (e.g., Ferroelectric Random Access Memory (FRAM)), an analog front-end controller (AFEC), an analog-to-digital converter (ADC), heating control circuitry, and/or the like. In various embodiments, the second component (e.g., the non-disposable component) 1703 (e.g., PCBA 1703A) may be electrically connected to the first component (e.g., the disposable component) 1705 (e.g., PCBA 1705A) to process electrical signals received from the first component (e.g., the disposable component) 1705 and/or to transfer outputs from the first component (e.g., the disposable component) 1705 into a particular output format. For example, circuitry of the second component (e.g., the non-disposable component) 1703 may be configured to format the output signal provided by the example first/disposable component 1705 into a ratio-metric output format, a current format, a digital output format and/or any other suitable format. In some cases, the circuitry of the second component (e.g., the non-disposable component) 1703 may be configured to provide an output to one or more electrical terminals facilitating electrical connections with electronic components of one or more apparatuses used in conjunction with the flow sensing assembly 1700. For example, the second component (e.g., the non-disposable component) 1703 may be in wired or wireless communication (e.g., Bluetooth) with an infusion pump. By way of example, when the first component (e.g., the disposable component) 1705 is electrically connected to the second component (e.g., the non-disposable component) 1703, the one or more memories of the second component (e.g., the non-disposable component) 1703 may be used by the second component (e.g., the non-disposable component) to generate necessary coefficients for compensation required by the first component (e.g., the disposable component) 1705. In one example, an electrical response to flowing media and temperature may be used to compensate for the temperature dependence of the first component (e.g., the disposable component) 1705 (e.g., a sensing element of the first component (e.g., a disposable component)). In some examples, as discussed herein, an example flow sensing assembly 1700 may comprise a heating element. In such examples, the second component (e.g., the non-disposable component) 1703 may comprise heating control circuitry/elements.

As noted above, the example flow sensing assembly 1700 comprises a first component (e.g., a disposable component) 1705. In some embodiments, as depicted, the first component (e.g., the disposable component) 1705 may be removably connected to the second component (e.g., the non-disposable component) 1703 via a securing element 1707. As depicted in FIG. 17, the flow sensing assembly 1700 comprises a securing element 1707 disposed on a surface of the flow sensing assembly 1700 for actuating release of the first component (e.g., the disposable component) 1705 from the second component (e.g., the non-disposable component) 1703. In some examples, as depicted, the securing element 1707 comprises a push button and spring-based mechanism 1709 for actuating release of the first component (e.g., the disposable component) 1705 from the second component (e.g., the non-disposable component) 1703.

In various embodiments, the first component (e.g., the disposable component) 1705 may comprise a sensing element. The example sensing element may be similar to the sensing element 205 described above in connection with FIG. 2. The example sensing element may be or comprise a MEMS sensor. The example sensing element may be at least partially disposed within a flow path of the example flow sensing device 1701. The example sensing element may comprise one or more circuitries, including, but not limited to, temperature sensing circuitry, communication circuitry (for example, near field communication (NFC) circuitry), and/or power control circuitry, and/or the like. The example first/disposable component 1705 may be in electronic communication with the second component (e.g., the non-disposable component) 1703.

While the description above provides an example flow sensing assembly 1700, it is noted that the scope of the present disclosure is not limited to the description above. In some examples, an example flow sensing assembly 1700 may in accordance with the present disclosure may be in other forms. In some examples, an example flow sensing assembly 1700 may comprise one or more additional and/or alternative elements, and/or may be structured/positioned differently than that illustrated in FIG. 17.

By way of example, flow sensing devices that convey flowing media (e.g., a flowing liquid) may be prone to having gas bubbles located within the flowing media or otherwise generated during operations. These gas bubbles may damage the example flow sensing devices as well as result in errors (e.g., inaccurate chemical compositions, incorrect delivery amounts, and/or the like). By way of example, in medical applications such as drug infusion pumps or pharmaceutical delivery systems, liquid medication may be provided to a human patient at a particular dosage such that the presence of any other material, debris, or gas bubble within these medical applications may result in incorrect dosages and/or, in some instances, damage to the human patient (e.g., embolisms or the like). Various attempts at addressing these issues require separate gas bubble detection modules (e.g., separate from the temperature sensors of the system) that may rely upon ultrasonic sensing technology or other non-invasive techniques that are often prone to false alarms (e.g., inaccurate results).

To solve these issues and others, example implementations of embodiments of the present disclosure may provide a heating element and/or temperature sensor configuration that may detect the presence of an example bubble based at least in part on an output of the heating element. Additionally, temperature data for at least two temperature sensors thermally coupled with a fluid flow system may be used to detect the presence of an gas bubble. Accordingly, such example implementations may reliably detect and confirm the presence of gas bubbles in fluid flow systems without additional detection components.

In various embodiments, an example flow sensing device may comprise a heating element to introduce thermal energy into the flowing media that can be detected by a temperature sensitive transducer. The example heating element may be or comprise a high-temperature coefficient of resistance (TCR) material (e.g., Pt, NiFe, doped silicon/polysilicon, PtSi and other silicides, W, AlN, WN or the like). Therefore, temperature control of the example heating element is critical for optimization for media type and temperature conditions. In some examples, a heater control circuit may be used in conjunction with a flow sensing device to generate a signal indicative of a sensitivity to media flow. In various examples, a sensing element's (e.g., thermocouples, thermopiles, High-TCR resistors and the like) energy may be transferred directly into a flowing media. By incorporating temperature feedback, temperature compensation for example sensing elements (e.g., transducers) may be provided. Additionally, a measure of the power output of the example heating element may be correlated to the measured media flow and media type. Accordingly, the output of the heating element may be adjusted to improve the resolution of motion of the flowing media. In a flow sensing device where the flowing media fluid is a liquid, a change from a liquid to a gas may induce a measurable change in the thermal properties detected adjacent the example heating element.

Figure 18:
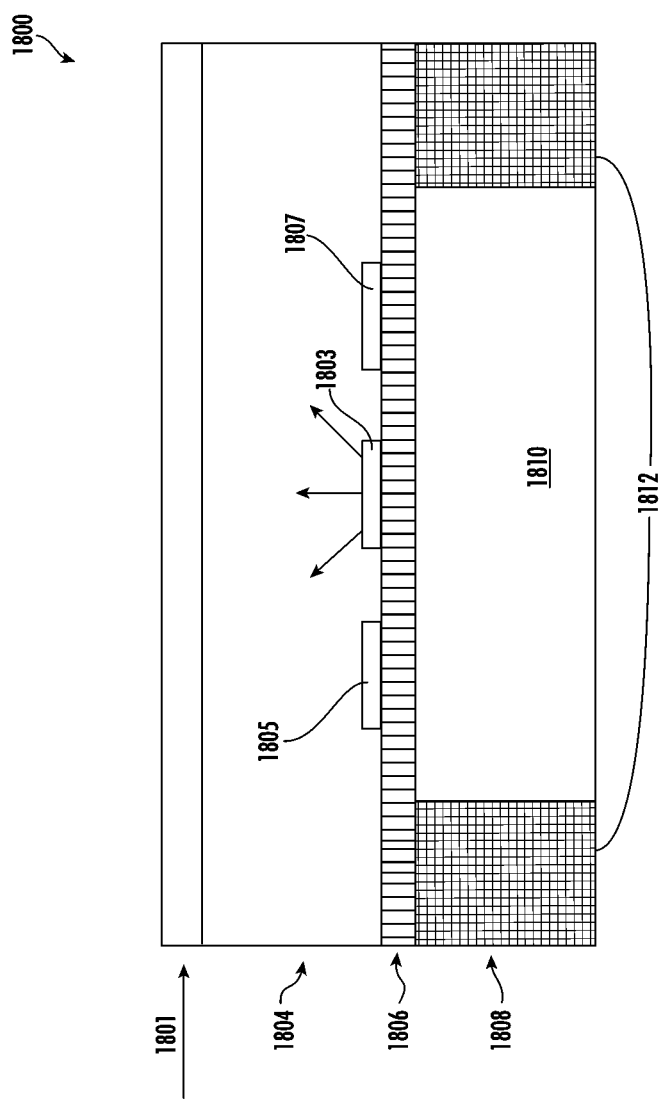
FIG. 18 illustrates a cross-sectional view of an example flow sensing device, in accordance with examples of the present disclosure.

Referring now to FIG. 18, a side section view depicting an example portion of a flow sensing assembly 1800 in accordance with various embodiments of the present disclosure is provided. In particular, as depicted, the example flow sensing assembly 1800 defines at least a portion of a flow sensing device 1804, a heating element 1803, a first temperature sensor 1805 and a second temperature sensor 1807. The flow sensing assembly 1800 may be similar to the flow sensing assembly 1500 described above in connection with FIG. 15. By way of example, the flow sensing assembly 1800 may define a housing or other enclosure configured to at least partially support one or more of the first temperature sensor 1805, the second temperature sensor 1807, and/or the heating element 1803. The first temperature sensor 1805, the second temperature sensor 1807, and the heating element 1803 may be in thermal engagement with a flowing media disposed within the at least a portion of the flow sensing device 18044. As depicted, the example flow sensing assembly 1800 comprises a plurality of layers/substrates which, in some examples, may define a unitary body. As shown, the example portion of the flow sensing device 1804 defines a sensing region. As further depicted, an upper substrate 1806 is disposed beneath the portion of the flow sensing device 1804 and a lower substrate 1808 disposed beneath the upper substrate 1806. As depicted, a top surface of the flow sensing device 1804 may define a top surface/region of the flow sensing assembly 1800. In various embodiments, an overcoat silicon nitride layer may isolates the heating element 1803 and the and the temperature sensors 1805 and 1807 from a flowing media.

An example gas bubble may propagate through the example flow sensing device 1804 in a particular direction. As depicted, the gas bubble may propagate through the example flow sensing device along a flow path 1801. As the gas bubble moves through the flow sensing device 1804, the first temperature sensor 1805 and/or the second temperature sensor 1807 may detect a change in temperature proximate the respective first and second temperature sensors 1805 and 1807 due to a thermal conductivity change within the example flow sensing device 1804 (e.g., the thermal conductivity of a liquid flowing media may be greater than that of the example gas bubble).

As depicted in FIG. 18, the example flow sensing assembly 1800 comprises a flow sensing device 1804. As depicted, at least a portion of the flow sensing device 1804 may define a top surface of the flow sensing assembly 1800. The flow sensing device 1804 may be similar to the flow sensing device 1501 described above in connection with FIG. 15. The flow sensing device 1804 may be or comprise a tubular shaped member configured to convey a flowing media therethrough (e.g., from an inlet to an outlet of the flow sensing device 1804). In various embodiments, the flow sensing device 1501 may form part of and/or be connected to an external flow channel such that a flowing media can be conveyed therethrough.

As depicted in FIG. 18, the example flow sensing assembly 1800 comprises a heating element 1803. In some examples, as depicted, the heating element 1803 may be disposed within the sensing region of the flow sensing device 1804/flow sensing assembly 1800. In various examples, the heating element 1803 and the temperature sensors 1805 and 1807 may be contained within a film stack. In some examples, as depicted, the heating element 1803 may be disposed (e.g., centrally) on the upper substrate 1806 (e.g., membrane) of the flow sensing assembly 1800 beneath the flow sensing device 1804. As further depicted, a central portion of the the lower substrate 1808 may define a cavity 1810 (e.g., a dry etched cavity). Additionally, at least a portion of the upper substrate 1806 may be disposed on at least a portion of the lower substrate 1808 (e.g., a silicon wafer 1812), for example, defining a supporting ring therebeneath. In various examples, the heating element 1803 may comprise any heat source configured to output thermal energy so as to heat or otherwise warm a flowing media within the flow sensing device 1804 proximate the heating element 1803. By way of example, the heating element may comprise a resistive heating element in which the passage of electrical current through a resistor produces heat. Although described herein with reference to a resistive heating element 1803, the present disclosure contemplates that any heating element (e.g., radiator, film heater, conductive heater, convective heater, etc.) may be used so as to generate a thermal output (e.g., generate heat). In various embodiments, flow sensing assembly 1800 further comprises a controller/heating control circuit that operates to maintain and/or control the thermal output of the heating element 1803. For example, the heating element 1803 may comprise a coil, a ribbon (including but not limited to, straight ribbon, corrugated ribbon), a plate, a wire strip, and/or a layer that may be connected to an electrical power source. In some examples, the heating element 1803 may comprise various geometries, including but not limited to a meander, a meander with rounded corner, an S-shaped, an S-shaped rounded corner, a double spiral, a double spiral with rounded corner, a double spiral with irregular spacings, a plane plate with central square hole, a circular, a drive wheel, an elliptical, a honeycomb, or an irregular. When the electrical power source is turned on, electric current may flow through the coil, the ribbon, the plate, the wire strip, and/or the layer, which may in turn convert electrical energy to heat energy.

The example heating element may be or comprise a high-temperature coefficient of resistance (TCR) material (e.g., Pt, NiFe, doped silicon/polysilicon, PtSi and other silicides, W, AlN, WN or the like). In some examples, the example heating element 1803 may comprise nickel-based and/or iron-based material. For example, the heating element 1803 may comprise one or more metal materials, such as nickel iron (NiFe) alloys, which may provide high temperature coefficients of electrical resistance. For example, the heating element 1803 may comprise 81% nickel (Ni) and 19% iron (Fe), Permalloy. Additionally, or alternatively, the heating element 1803 may comprise 60% Ni and 40% Fe. In some examples, the heating element 1803 may comprise platinum, e.g., platinum in the form of a thin film heater due to its high temperature coefficient of resistance (TCR). In some examples, copper alloys with low thermal conductivity, such as alloy, may also be used for the heating element 1803.

In some examples, the example controller/heating control circuit may operate so as to maintain a substantially (e.g., within applicable tolerances) constant thermal output of the heating element 1803. Said differently, in some examples, the flow sensing assembly 1800 may employ a heating element 1803 with a substantially constant thermal output so as to stabilize the temperature data detected/generated by the first temperature sensor 1805 and the second temperature sensor 1807. In various embodiments, the controller may be co-located or remote from the flow sensing assembly 1800.

As depicted in FIG. 18, the example flow sensing assembly 1800 comprises a first temperature sensor 1805 and a second temperature sensor 1807. In various examples, the first temperature sensor 1805 may be configured to generate first temperature data. As depicted, the first temperature sensor 1805 may be in thermal engagement with at least a portion of the flow sensing device 1804 (e.g., in thermal engagement with a flowing media within the flow sensing device 1804) so as to determine a temperature within the flow sensing device 1804 proximate the first temperature sensor 1805. In some embodiments, the first temperature sensor 1805 may be positioned upstream (e.g., relative the flow path 1801) of the heating element 1803 and the second temperature sensor 1807. By way of example, the first temperature sensor 1805 may include a thermocouple, positive temperature coefficient (PTC) thermistor, negative temperature coefficient (NTC) thermistor, -p-n junction, resistor, and/or the like configured to determine the temperature of the fluid proximate the first temperature sensor 1805. Although illustrated with a single first temperature sensor 1805, the present disclosure contemplates that the first temperature sensor 1805 may further comprise a pair of offset thermopiles configured to, alone or in combination, generate first temperature data. Said differently, although described herein with reference to a single first temperature sensor 1805 for convenience of description, the present disclosure contemplates that the techniques herein may be applicable to any number of first temperature sensors 1805 positioned at any location with respect to the flow sensing device 1804.

As further depicted in FIG. 18, the flow sensing assembly 1800 may include a second temperature sensor 1807 that may be configured to generate second temperature data. As shown, the second temperature sensor 1807 may be in thermal engagement with the flow sensing device 1804 (e.g., in thermal engagement with a flowing media within the flow sensing device 1804) so as to determine a temperature within the flow sensing device 1804 proximate the second temperature sensor 1807. In some embodiments, the second temperature sensor 1807 may be positioned downstream (e.g., relative the flow path 1801) of the heating element 1803 and the first temperature sensor 1805. By way of example, the second temperature sensor 1807 may also include a thermocouple, positive temperature coefficient (PTC) thermistor, negative temperature coefficient (NTC) thermistor, p-n junction, resistor, and/or the like configured to determine the temperature of the fluid proximate the second temperature sensor 1807. Although illustrated with a single second temperature sensor 1807, the present disclosure contemplates that the second temperature sensor 1807 may further comprise a pair of offset thermopiles configured to, alone or in combination, generate second temperature data. Said differently, although described herein with reference to a single second temperature sensor 1807 for convenience of description, the present disclosure contemplates that the techniques herein may be applicable to any number of second temperature sensors 1807 positioned at any location with respect to the flow sensing device 1804.

In some example embodiments, the first temperature sensor 1805 and/or the second temperature sensor 1807 (or their equivalent functionality) may be positioned on the heating element 1803. Said differently, the generation of temperature data as described herein may, in some embodiments, refer to temperature data generated near or on the heating element 1803. By way of example, as a gas bubble passes by or traverses proximate the heating element 1803, the resistance of the heating element 1803 may also change due, at least in part, to the differences in heat capacity and thermal conductivity between gases and liquids as described herein. As the example gas bubble moves over a heating element 1803 (e.g., a resistive heater) the temperature of the heating element 1803 may increase, and the heating element's 1803 resistance will change based on the temperature coefficient of resistance of the material of the heating element 1803.

While the description above provides some examples of temperature sensors, it is noted that the scope of the present disclosure is not limited to the description above. In some examples, an example temperature sensor may comprise one or more additional and/or alternative element(s), one or more additional and/or alternative material(s), and/or may be in other form(s). For example, an example temperature sensor may comprise at least one temperature sensing circuit, such as, but not limited to, resistors in a Wheatstone bridge circuit, or temperature sensitive diodes. In the example of a Wheatstone bridge circuit, two resistor branches may be provided, and each resistor branch may comprise two resistor elements. As temperature may affect the electrical resistance of the resistor element, an example temperature sensor may detect, measure, and/or identify the resistance change between the two resistor branches to determine the corresponding thermal energy.

While the description above provides an example flow sensing assembly 1800, it is noted that the scope of the present disclosure is not limited to the description above. In some examples, an example flow sensing assembly 1800 may in accordance with the present disclosure may be in other forms. In some examples, an example flow sensing assembly 1800 may comprise one or more additional and/or alternative elements, and/or may be structured/positioned differently than that illustrated in FIG. 18.

While the description above provides an example flow sensing assembly 1800 that comprises two temperature sensors, it is noted that the scope of the present disclosure is not limited to the description above. In some examples, an example sensor component may comprise less than two or more than two temperature sensors. In some examples, the flowing media may travel through a sensing region that may comprise the heating element 1803, the first temperature sensor 1805 and the second temperature sensor 1807. For example, the first temperature sensor 1805 may be positioned in an upstream direction relative to the heating element 1803. The second temperature sensor 1807 may be positioned in a downstream direction relative to the heating element 1803. In such examples, the first temperature sensor 1805 may detect a first temperature of the flowing media. Subsequently, the flowing media may be heated by the heating element 1803, which may increase the temperature of the flowing media by a predetermined amount. Subsequently, the second temperature sensor 1807 may detect a second temperature of the flowing media. As the flow rate of the flowing media increases, more heat may be lost as the flowing media travels from the heating element 1803 to the second temperature sensor 1807. By comparing the difference between the first temperature and the second temperature with the predetermined amount, a flow rate of the flowing media may be calculated.

In some examples, the distance that temperature sensors are spaced from the heating element may be chosen in order to achieve an acceptable accuracy of flow rate measurements across an acceptably wide range of flow rates and/or for a desired range of flow rates (e.g., low flow rates between about 1 µL/hour and about 10,000 µL/hour). In some embodiments, the number of temperature sensors may also be chosen such that the accuracy of flow rate measurement for a desired flow rate range is achieved. In some examples, using only a single temperature sensor may lead to a tailing off of accuracy or precision at some flow rates, such as low flow rates. In some examples, using two temperature sensors spaced at different distances from the heating element may lead to an increased accuracy at low flow rates or the like. Without wishing to be bound by any particular theory, the increased accuracy or precision at low flow rates or the like may be due to differences in peak accuracy for a closer temperature sensor and peak accuracy for a further temperature sensor. In some examples, a closer temperature sensor may be more well suited for accurate and/or precise measurement of higher flow rates since a higher flow rate of media may increase the heat sink capacity of the media in the flow path of the example flow sensing device. In some examples, a further temperature sensor may be more well suited for accurate and/or precise measurement of lower flow rates since a lower flow rate of media may decrease the heat sink capability of the media and differences in temperature may be more easily detected by the further positioned temperature sensor.

In some examples, when temperature sensors comprise thermopiles made up of a plurality of thermocouples, it may be helpful to use more thermocouples in a thermopile because the use of more thermocouples may increase the sensitivity of thermopile to temperature changes, which can increase the sensitivity of the flow rate sensor. In some examples, e.g., for a digital sensor, this can improve accuracy in a number of bits that represent a measured voltage value.

While the description above provides some examples of temperature sensors, it is noted that the scope of the present disclosure is not limited to the description above. In some examples, an example temperature sensor may comprise one or more additional and/or alternative element(s), one or more additional and/or alternative material(s), and/or may be in other form(s). For example, an example temperature sensor may comprise at least one temperature sensing circuit, such as, but not limited to, resistors in a Wheatstone bridge circuit, or temperature sensitive diodes.

In some examples, temperature sensors may be disposed in a separate layer of the sensor component from the layer in which the heating element is located. In some examples, the separate layer of the sensor component comprising temperature sensors may comprise one or more suitable material(s), including but not limited to, silicon nitride, silicon oxide, silicon oxynitride, a polymer, or other electrically insulating thin films. In some examples, the separate layer of the sensor component comprising temperature sensors may be an encapsulating layer that may protect temperature sensors, which may comprise metals that may be corroded by moisture and other chemicals. In some examples, the encapsulating layer may be electrically insulating.

In some examples, temperature sensors may be electronically coupled to one or more other elements (for example, an electrical power source, a processor) based on techniques such as, but not limited to, through-glass via (TGV), through-silicon via (TSV), and/or aerosol or ink jet printing. Additionally, or alternatively, temperature sensors may be electronically coupled to one or more other elements through other means.

Figure 19:
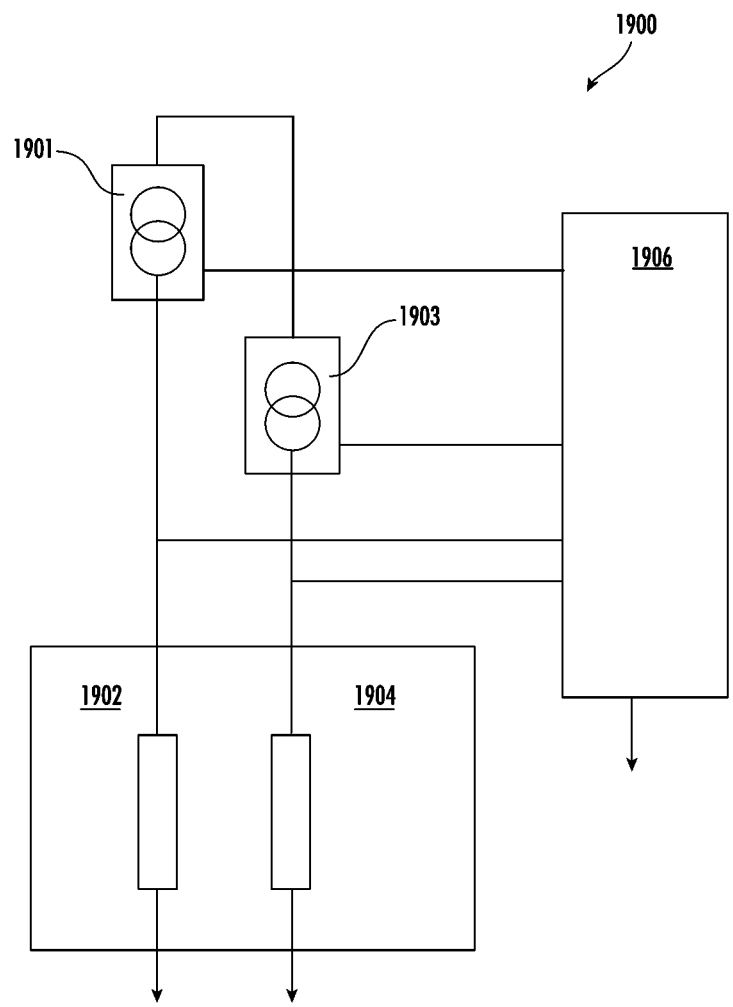
FIG. 19 illustrates a schematic diagram of an example heating control circuit, in accordance with examples of the present disclosure.

Referring now to FIG. 19, a schematic diagram depicting an example heater control circuit 1900/controller in accordance with various embodiments of the present disclosure is provided. In particular, as depicted, the example heater control circuit comprises a first current source 1901, a second current source 1903, a first sense resistor 1902, a second sense resistor 1904, and a controller element 1906. In various embodiments, the heater control circuit 1900 is configured to monitor and control one or more operations/functions of an example heating element. The example heating element may be similar to the heating element 1803 described above in connection with FIG. 18. By way of example, the heating control circuit 1900 may be configured to regulate a current/power output associated with the example heating element.

As depicted in FIG. 19, the example heater control circuit comprises a first current source 1901 and a second current source 1903. In some examples, each of the first current source 1901 and a second current source 1903 may be or comprise an adjustable current source such as a high-side DAC or p-channel device. As further depicted in FIG. 19, each of the first current source 1901 and a second current source 1903 may be electrically connected to the first sense resistor 1902 and the second sense resistor 1904, respectively.

In various embodiments, the first sense resistor 1902 may be configured to detect a temperature proximate the heating element and the second sense resistor 1904 may be configured to detect an ambient temperature (e.g., temperature of a silicon substrate). In various embodiments, the first current source 1901 and a second current source 1903 operate to maintain a predetermined temperature by the heating element. In various embodiments, the heater control circuit 1900 may operate to calibrate the temperature adjacent (e.g., directly above) the example heating element. Additionally, as depicted, the heating control circuit 1900 may comprise a controller element 1906 configured to store and/or adjust operational parameters of the system based on detected conditions. Example conditions may comprise, for example without limitation, power absorbed by an example media, ambient temperature, a difference between first temperature data (e.g., associated with a first temperature sensor located upstream of an example heating element) and second temperature data (e.g., associated with a first temperature sensor located downstream of an example heating element).

In some examples, the heater control circuit 1900 may be configured to determine a type of flowing media disposed within a flow path directly above the heating element based on detecting an output of the example heating element. By way of example, because the heating element may be configured to maintain a predetermined temperature, it may increase its power output in response to characteristics of the flowing media disposed within the flow path of the example flow sensing device. Said differently, the first current source 1901 and a second current source 1903 may operate to maintain a predetermined system temperature by the example heating element. In one example, if a flowing media disposed directly above the example heating element is liquid, a detected output (e.g., voltage output) of the heating element may differ from when the flowing media disposed directly above the heating element is air. Accordingly, by monitoring the output of the heating element (e.g., voltage output) which may vary based on the media disposed within the flow path directly above the heating element and/or in conjunction with temperature data from one or more locations relative to the heating element (e.g., adjacent the first temperature sensor and the second temperature sensor), a media type can be determined based on the output of the example heating element.

Figure 20:
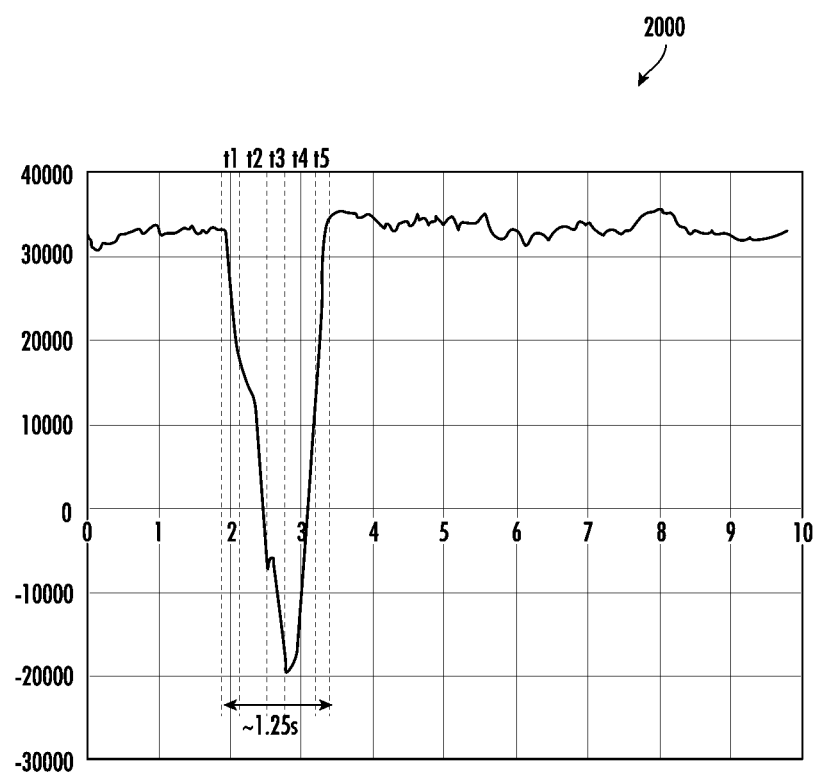
FIG. 20 illustrates a graphical representation depicting experimental results, in accordance with examples of the present disclosure.

Referring now to FIG. 20, an example graphical representation 2000 depicting experimental results with respect to an example flow sensing assembly comprising a heating element. As depicted in FIG. 20, the x-axis depicts time and the y-axis depicts a digital voltage output (e.g., digital counts) associated with an example temperature sensor element in response to the example heating element. In various examples, as an example bubble traverses an example flow path, (e.g., from a first location adjacent a first temperature sensor to a second location adjacent a second temperature sensor) the output of the heating element will vary based on characteristics of the bubble (e.g., curvature, size and the like). As depicted in FIG. 20, in the first portion of the graph, the voltage output of the example heating element may be substantially constant. As depicted, for a duration of 1.25 seconds, indicated as phases t1 and t5, an example bubble traverses a flow path adjacent (e.g., directly above) the heating element. As depicted in FIG. 20, the output of the example heating element may change between phases t1 and t5 due to the presence of an example bubble traversing the flow path adjacent (e.g., directly above) the example heating element. As depicted, during phase t1, a detected voltage output signal falls significantly (e.g., as a leading edge of the example bubble is disposed adjacent the first temperature sensor). As depicted, during phase t2, the detected voltage output signal continues to fall (e.g., as a leading edge of the example bubble is disposed adjacent the heating element). As depicted, during phases t3 and t4, the detected voltage output signal may overshoot (e.g., as the leading edge of the example bubble moves beyond the heating element and is disposed adjacent the second temperature sensor). As depicted, during phase t5, the detected voltage output signal may increase (e.g., as the flowing media transitions from the example bubble to a liquid and moves away from the sensing region of the example flow sensing device). Accordingly, by monitoring the output of the heating element, an example bubble may be detected. Additionally, as described herein, the architecture of the example bubble may correspond with the detected output over a period of time. For example, as depicted an example bubble of a particular size (e.g., as depicted 170 μL) may be associated with a defined period of time (e.g., 1.25 s) for a particular flow rate (e.g., 500 ml/hr) such that the size of any other example bubble may be determined. As such, a bubble size and/or curvature can be determined by monitoring an output of the heating element without stopping operations of the heating element and flow sensing device. In various embodiments, data/information associated with detected bubbles may be provided to higher levels of the system (e.g., integrated with a controller such as, but not limited to, an ASIC).

Described herein are operations performed in accordance with example embodiments of the present disclosure. It will be understood that each operation, and combinations of operations, may be implemented by various means, such as devices comprising hardware, firmware, one or more processors, and/or circuitry associated with execution of software comprising one or more computer program instructions. In some embodiments, one or more of the procedures described above may be performed by execution of program code instructions. For example, one or more of the procedures described above may be performed by material handling equipment (e.g., a robotic arm, servo motor, motion controllers, and the like) and computer program instructions residing on a non-transitory computer-readable storage memory. In this regard, the program code instructions that, when executed, cause performance of the procedures described above may be stored by a non-transitory computer-readable storage medium (e.g., memory) of a computing apparatus and executed by a processor of the computing apparatus. In this regard, the computer program instructions which embody the procedures described above may be stored by a memory of an apparatus employing an embodiment of the present disclosure and executed by a processor of the apparatus. As will be appreciated, any such computer program instructions may be loaded onto a computer or other programmable apparatus (e.g., hardware) to produce a machine, such that the resulting computer or other programmable apparatus provides for implementation of the functions specified throughout the present application. When executed, the instructions stored in the computer-readable storage memory produce an article of manufacture configured to implement the various functions specified throughout the present application. The program code instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the operations described throughout the present application. Moreover, execution of a computer or other processing circuitry to perform various functions converts the computer or other processing circuitry into a particular machine configured to perform an example embodiment of the present disclosure.

Operations and processes described herein support combinations of means for performing the specified functions and combinations of operations for performing the specified functions. It will be understood that one or more operations, and combinations of operations, may be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method and process descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," and similar words are not intended to limit the order of the steps; these words are simply used to guide the reader through the description of the methods. Further, any reference to claim elements in the singular, for example, using the articles "a," "an" or "the," is not to be construed as limiting the element to the singular and may, in some instances, be construed in the plural.

As described above and as will be appreciated based on this disclosure, embodiments of the present disclosure may be configured as systems, apparatuses, methods, mobile devices, backend network devices, computer program products, other suitable devices, and combinations thereof. Accordingly, embodiments may comprise various means including entirely of hardware or any combination of software with hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices. As will be appreciated, any computer program instructions and/or other type of code described herein may be loaded onto a computer, processor or other programmable apparatus' circuitry to produce a machine, such that the computer, processor, or other programmable circuitry that executes the code on the machine creates the means for implementing various functions, including those described herein. In some embodiments, features of the present disclosure may comprise, or be communicatively coupled to, an application specific integrated circuit (ASIC) configured to convert the differential output voltage from thermopile or thermopiles (e.g., either in a single chip or two-chip configuration).

While various embodiments in accordance with the principles disclosed herein have been shown and described above, modifications thereof may be made by one skilled in the art without departing from the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present disclosure. Furthermore, any advantages and features described above may relate to specific embodiments, but shall not limit the application of such issued claims to processes and structures accomplishing any or all of the above advantages or having any or all of the above features.

In addition, the section headings used herein are provided for consistency with the suggestions under 37 C.F.R. § 1.77 or to otherwise provide organizational cues. These headings shall not limit or characterize the disclosure set out in any claims that may issue from this disclosure. For instance, a description of a technology in the "Background" is not to be construed as an admission that certain technology is prior art to any disclosure in this disclosure. Neither is the "Summary" to be considered as a limiting characterization of the disclosure set forth in issued claims. Furthermore, any reference in this disclosure to "disclosure" or "embodiment" in the singular should not be used to argue that there is only a single point of novelty in this disclosure. Multiple embodiments of the present disclosure may be set forth according to the limitations of the multiple claims issuing from this disclosure, and such claims accordingly define the disclosure, and their equivalents, that are protected thereby. In all instances, the scope of the claims shall be considered on their own merits in light of this disclosure, but should not be constrained by the headings set forth herein.

Also, systems, subsystems, apparatuses, techniques, and methods described and illustrated in the various embodiments as discrete or separate may be combined or integrated with other systems, modules, techniques, or methods without departing from the scope of the present disclosure. Other devices or components shown or discussed as coupled to, or in communication with, each other may be indirectly coupled through some intermediate device or component, whether electrically, mechanically, or otherwise. Other examples of changes, substitutions, and alterations are ascertainable by one skilled in the art and could be made without departing from the scope disclosed herein.

Many modifications and other embodiments of the disclosure set forth herein will come to mind to one skilled in the art to which these embodiments pertain having the benefit of teachings presented in the foregoing descriptions and the associated figures. Although the figures only show certain components of the apparatuses and systems described herein, various other components may be used in conjunction with the components and structures disclosed herein. Therefore, it is to be understood that the disclosure is not to be limited to the specific embodiments disclosed and that modifications and other embodiments are intended to be included within the scope of the appended claims. For example, the various elements or components may be combined, rearranged, or integrated in another system or certain features may be omitted or not implemented. Moreover, the steps in any method described above may not necessarily occur in the order depicted in the accompanying drawings, and in some cases one or more of the steps depicted may occur substantially simultaneously, or additional steps may be involved. Although specific terms are employed herein, they are used in a generic and descriptive sense only and not for purposes of limitation.

The invention claimed is:

1. A flow sensing device comprising:
   a housing;
   a sensing element disposed at least partially within the housing;
   a shielding element, wherein at least a portion of the shielding element is in direct contact with at least a portion of the sensing element;
   a plurality of channels disposed within the housing defining a flow path configured to convey a flowing media through the flow sensing device, wherein the flow path is disposed proximate the sensing element such that at least a portion of the flowing media makes direct contact with the sensing element;
   wherein at least a portion of the housing defines a barrier wall disposed adjacent a surface of the sensing element, wherein the barrier wall is configured to isolate wire bonds of the sensing element from the flowing media, wherein the shielding element comprises a fin for laminarizing and directing a flow of a flowing medium within at least one channel of the flow sensing device.

2. The flow sensing device of claim 1, further comprising a printed circuit board assembly (PCBA) in electronic communication with the sensing element.

3. The flow sensing device of claim 1, wherein at least a portion of plurality of channels defines an angular, non-planar geometry.

4. The flow sensing device of claim 2, wherein the shielding element is at least partially disposed between a surface of the housing, a surface of the PCBA and the surface of the sensing element.

5. The flow sensing device of claim 2, wherein the PCBA and the sensing element are connected via the wire bonds, and wherein the wire bonds are covered in an encapsulant material.

6. The flow sensing device of claim 1, further comprising a heating element configured to provide a thermal output to the flowing media.

* * * * *